US010799635B2

(12) United States Patent
Carlsson et al.

(10) Patent No.: US 10,799,635 B2
(45) Date of Patent: Oct. 13, 2020

(54) MONITORING UNIT

(71) Applicant: CAREBAY EUROPE LTD, Sliema (MT)

(72) Inventors: Daniel Carlsson, Enskede (SE); Daniel Säll, Segeltorp (SE); Nikolaj Hautaviita, Bro (SE)

(73) Assignee: SHL MEDICAL AG, Zug (CH)

( * ) Notice: Subject to any disclaimer, the term of this patent is extended or adjusted under 35 U.S.C. 154(b) by 128 days.

(21) Appl. No.: 16/080,748

(22) PCT Filed: Mar. 6, 2017

(86) PCT No.: PCT/EP2017/055173
§ 371 (c)(1),
(2) Date: Aug. 29, 2018

(87) PCT Pub. No.: WO2017/162420
PCT Pub. Date: Sep. 28, 2017

(65) Prior Publication Data
US 2019/0022320 A1    Jan. 24, 2019

(30) Foreign Application Priority Data

Mar. 22, 2016  (EP) .................................... 16161584

(51) Int. Cl.
*A61M 5/20* (2006.01)
*A61M 5/32* (2006.01)

(52) U.S. Cl.
CPC .......... *A61M 5/2033* (2013.01); *A61M 5/326* (2013.01); *A61M 2005/2013* (2013.01);
(Continued)

(58) Field of Classification Search
CPC .................. A61M 5/2033; A61M 5/20; A61M 2205/3553; A61M 2205/3569;
(Continued)

(56) References Cited

U.S. PATENT DOCUMENTS

2016/0166761 A1*  6/2016  Piehl ................... A61M 5/1408
604/506

FOREIGN PATENT DOCUMENTS

CN       103702699 A      4/2014
CN       104220116 A     12/2014
(Continued)

OTHER PUBLICATIONS

International Search Report and Written Opinion for Int. App. No. PCT/EP2017/055173, dated Apr. 13, 2017.
(Continued)

*Primary Examiner* — Kevin C Sirmons
*Assistant Examiner* — Alexandra Lalonde
(74) *Attorney, Agent, or Firm* — McDonnell Boehnen Hulbert & Berghoff LLP

(57) ABSTRACT

The present disclosure relates to a monitoring unit for a medicament delivery device, where the monitoring unit has a housing, monitoring circuit arranged in the housing, capable of detecting and monitoring functions of the medicament delivery device, releasable holding elements, which releasable holding elements interact with a medicament delivery device for releasably holding the monitoring unit when attached to a medicament delivery device. Locking elements are operably arranged in the monitoring unit to act on the attachment mechanism, and at least one drive element is operably connected to the locking elements wherein, upon activation of the monitoring unit, the at least one drive element causes the locking elements to act on the releasable holding elements, preventing detachment of said monitoring unit from the medicament delivery device.

20 Claims, 17 Drawing Sheets

(52) U.S. Cl.
CPC ........... *A61M 2005/3247* (2013.01); *A61M 2005/3267* (2013.01); *A61M 2205/3553* (2013.01); *A61M 2205/3561* (2013.01); *A61M 2205/3569* (2013.01); *A61M 2205/3592* (2013.01)

(58) Field of Classification Search
CPC .. A61M 2205/3592; A61M 2205/6045; A61M 2005/2006; A61M 2005/2013; A61M 2205/3561; A61M 2205/3327; A61M 5/1413; A61M 5/31546; A61M 2005/3142
See application file for complete search history.

(56) References Cited

FOREIGN PATENT DOCUMENTS

| CN | 105102024 | A | 11/2015 | | |
|---|---|---|---|---|---|
| CN | 105120929 | A | 12/2015 | | |
| EP | 2814545 | A1 | 12/2014 | | |
| WO | 2013/120775 | A1 | 8/2013 | | |
| WO | 2013/120777 | A1 | 8/2013 | | |
| WO | 2014/020008 | A1 | 2/2014 | | |
| WO | 2014/128156 | A1 | 8/2014 | | |
| WO | 2014/173773 | A1 | 10/2014 | | |
| WO | WO-2014173773 | A1 * | 10/2014 | ........ | A61M 5/31535 |
| WO | 2015/185687 | A1 | 12/2015 | | |

OTHER PUBLICATIONS

Chinese Office Action for CN App. No. 2017800168165, dated May 6, 2020.

European Office Action for EP App. No. 17708804.4, dated Mar. 18, 2020.

* cited by examiner

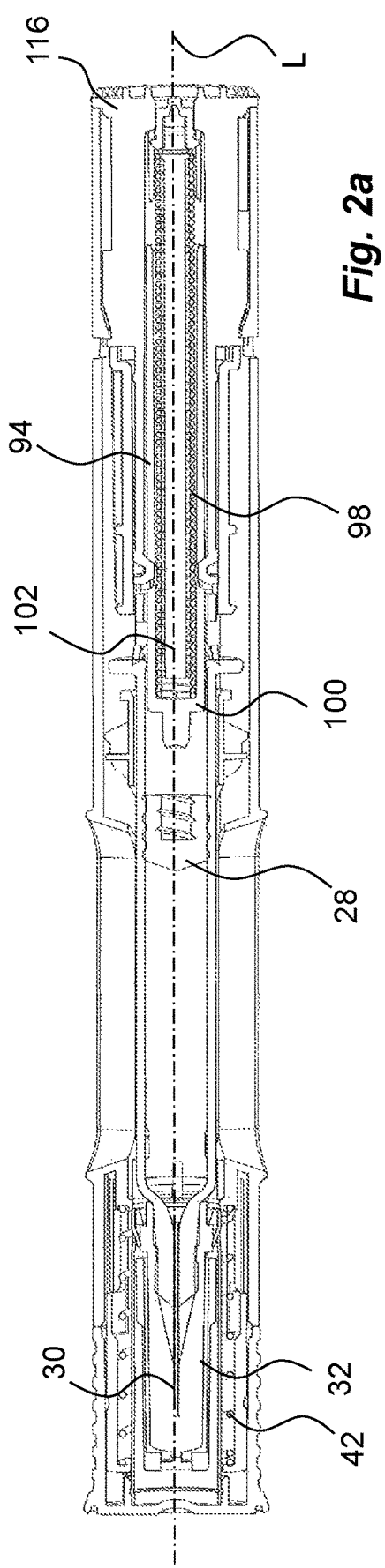
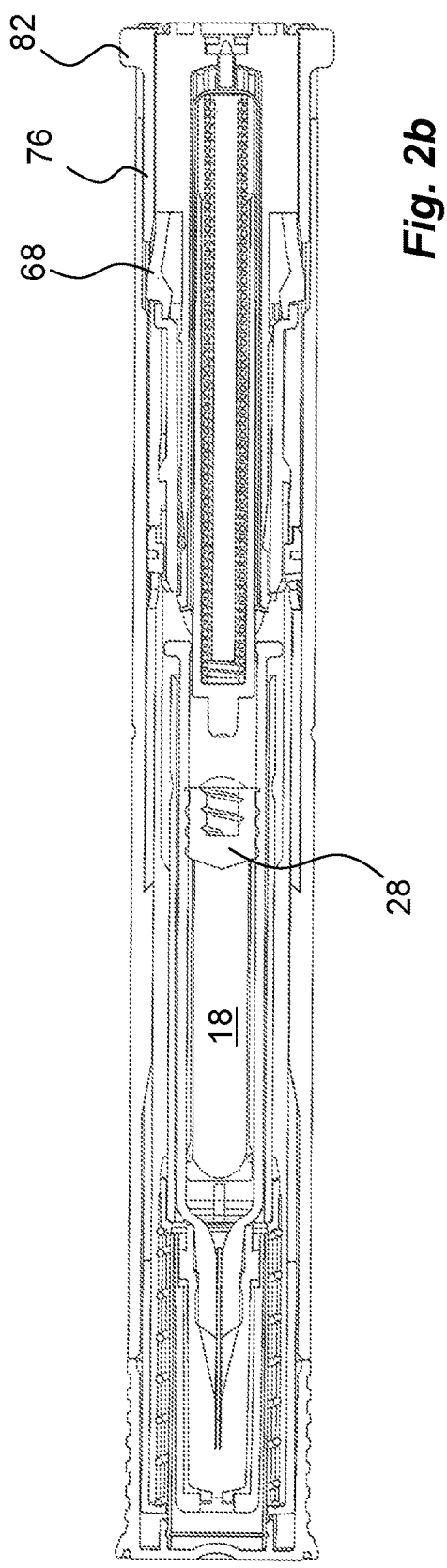
Fig. 2a
Fig. 2b

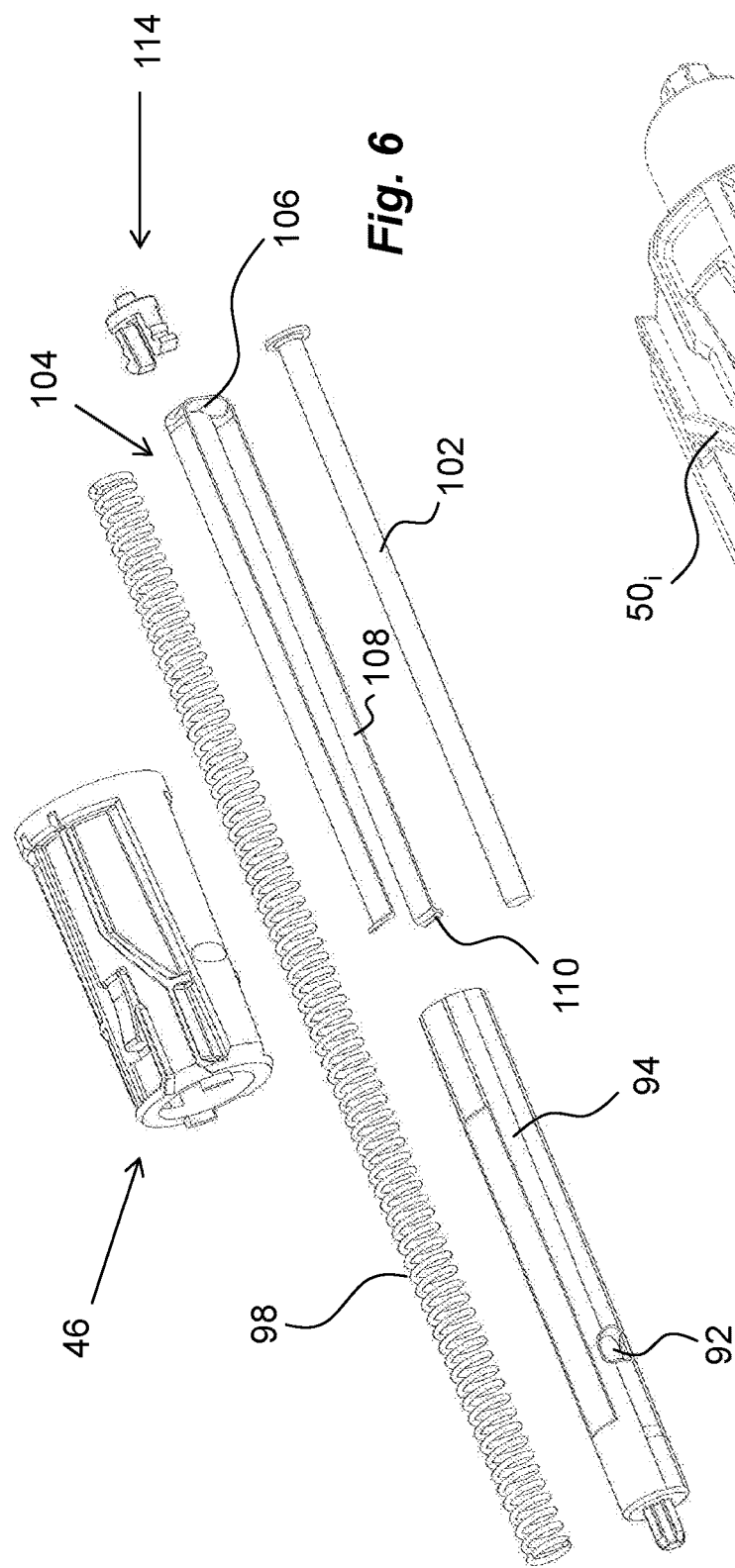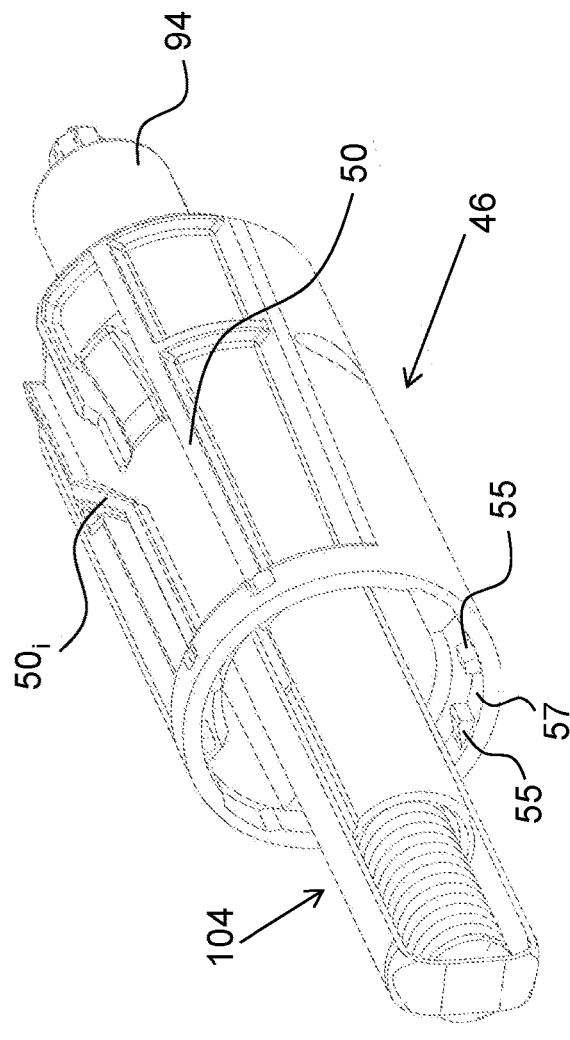

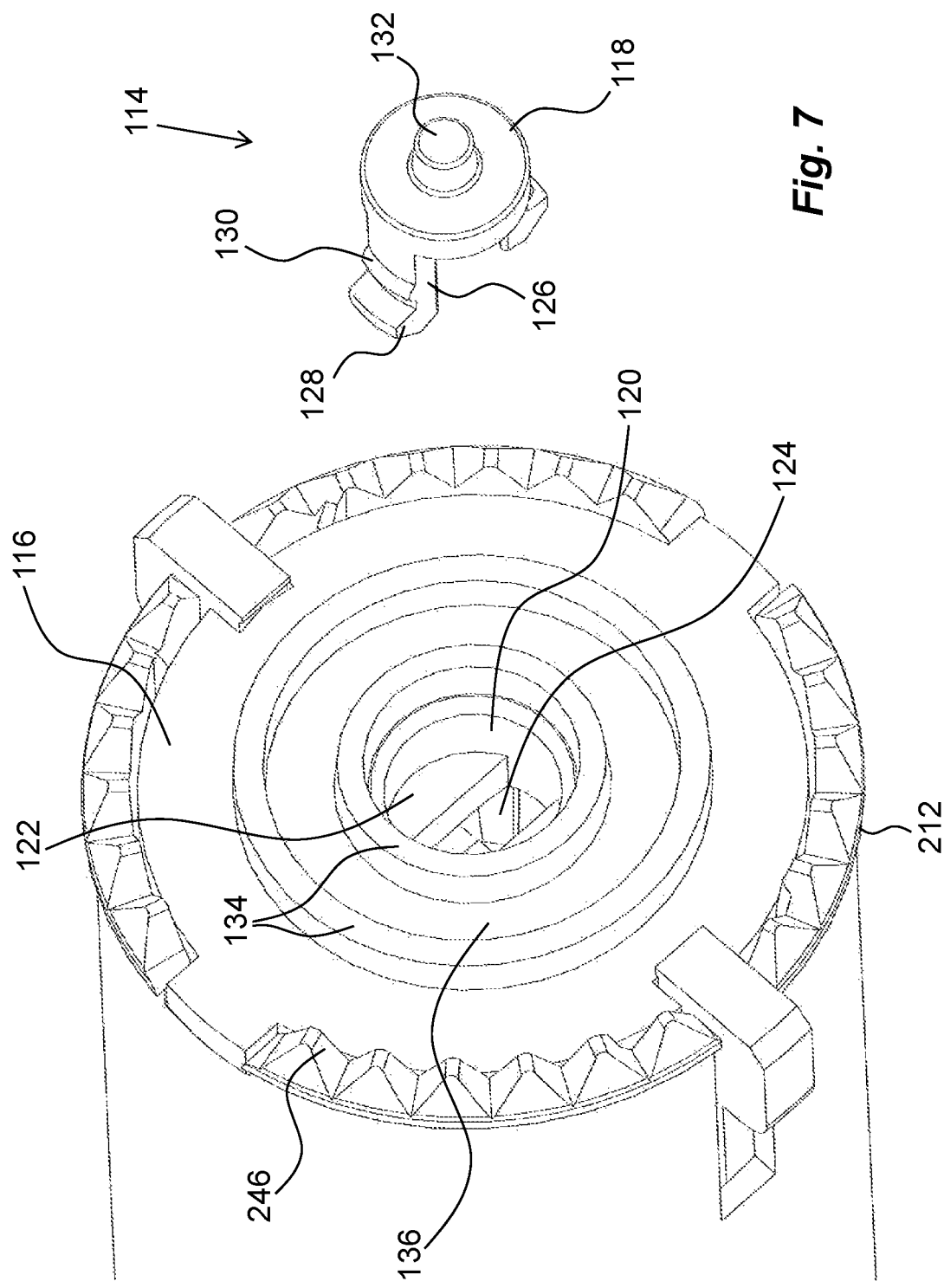

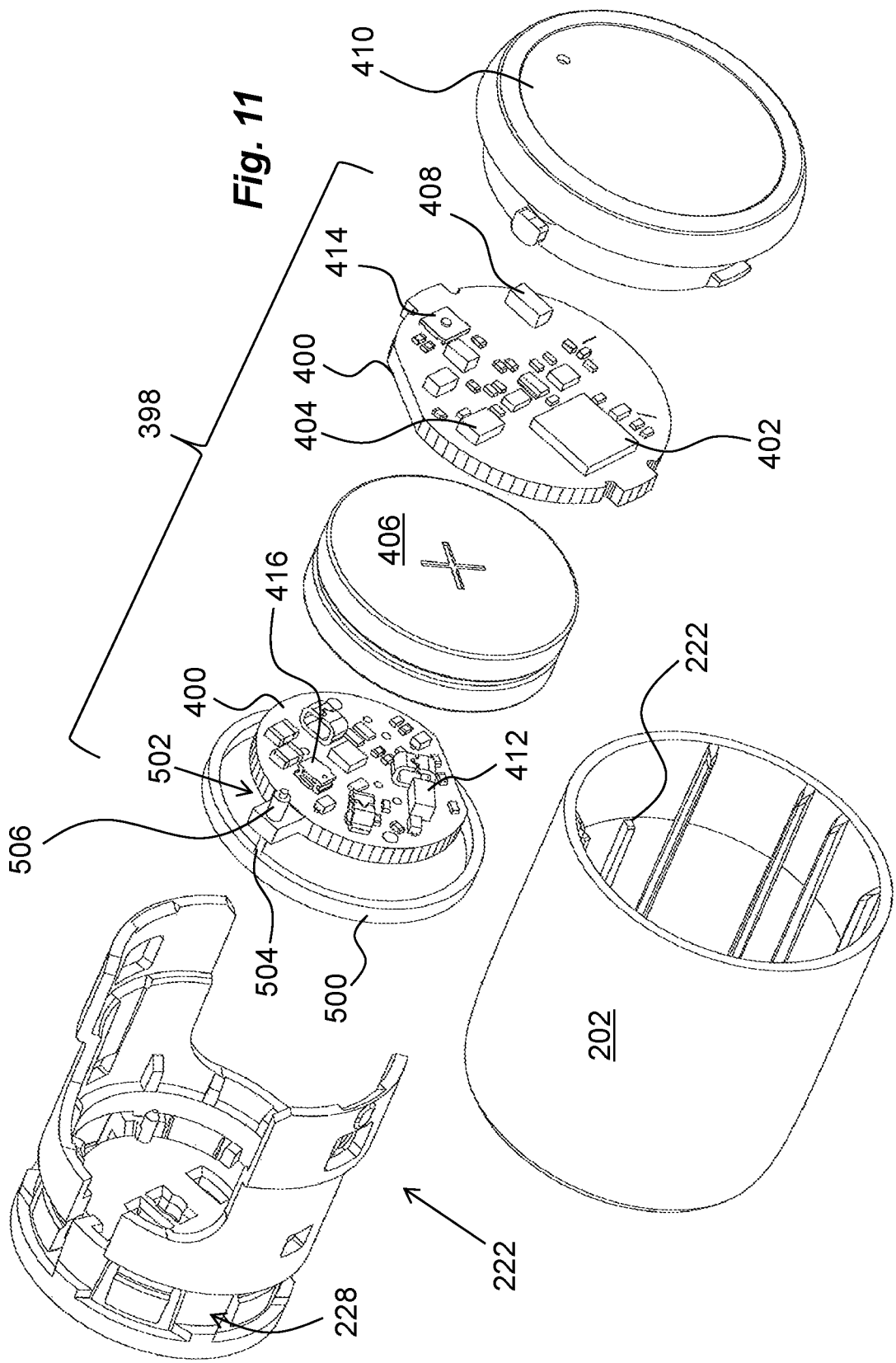

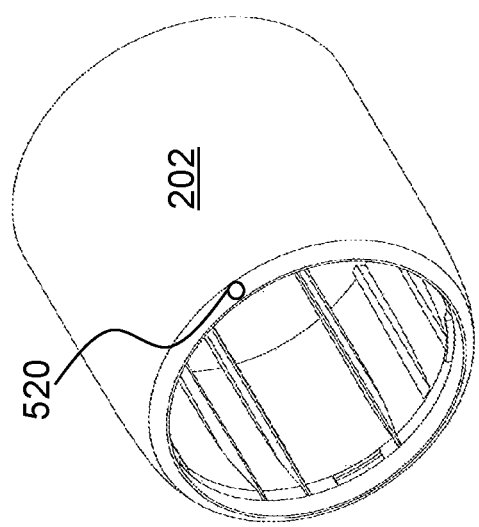
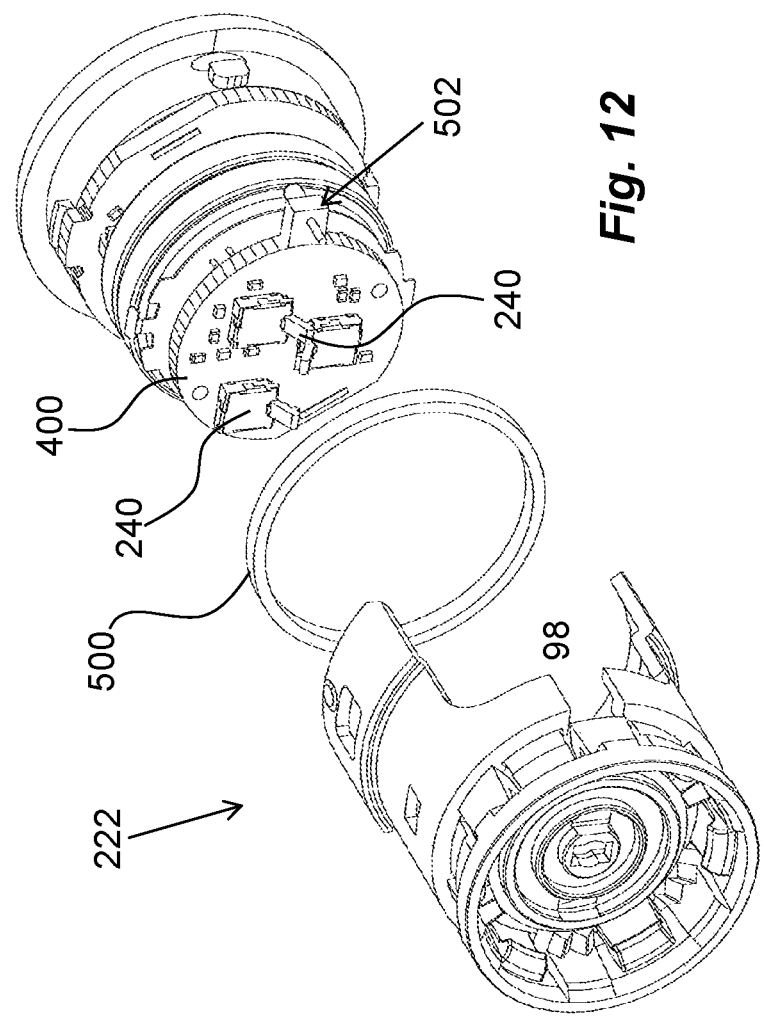
Fig. 12

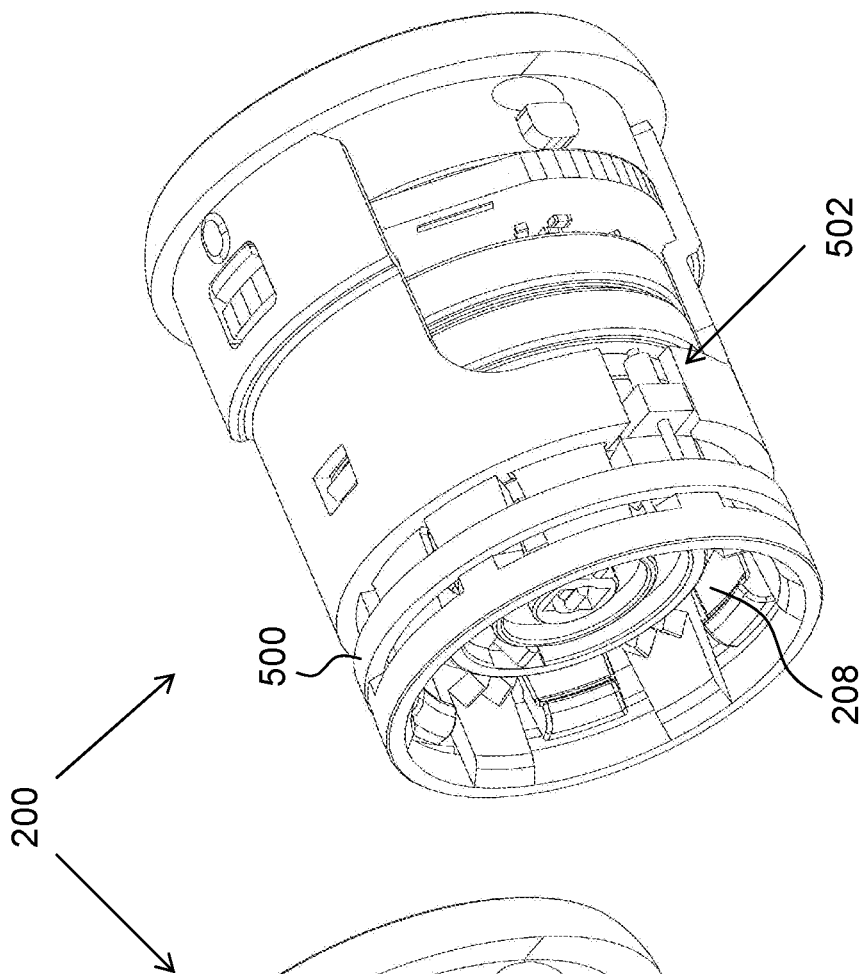
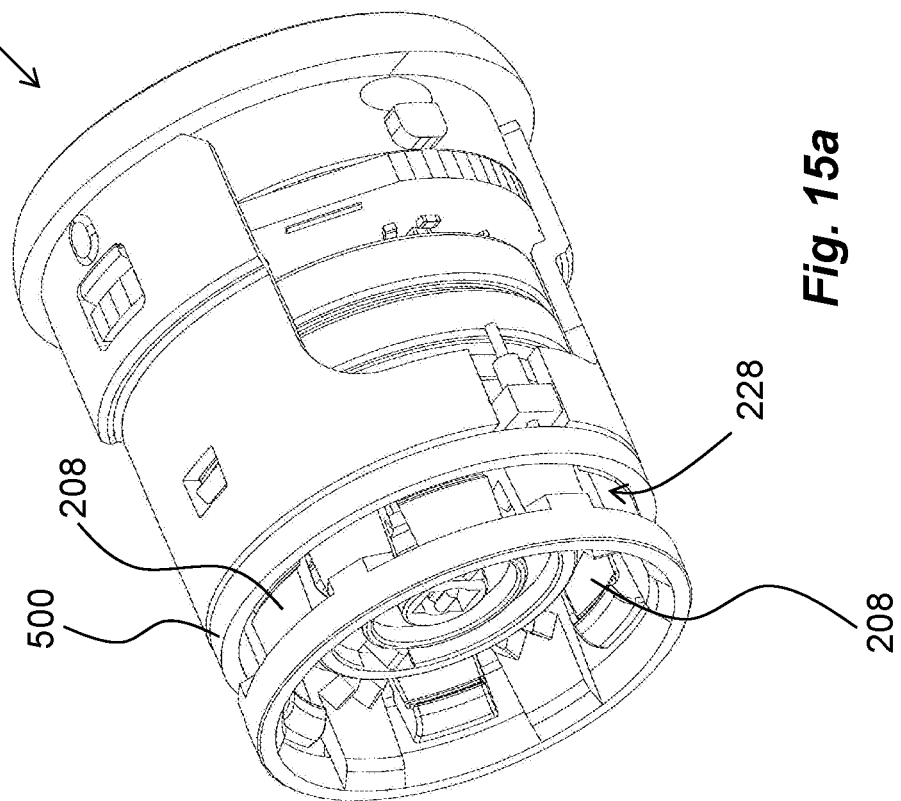

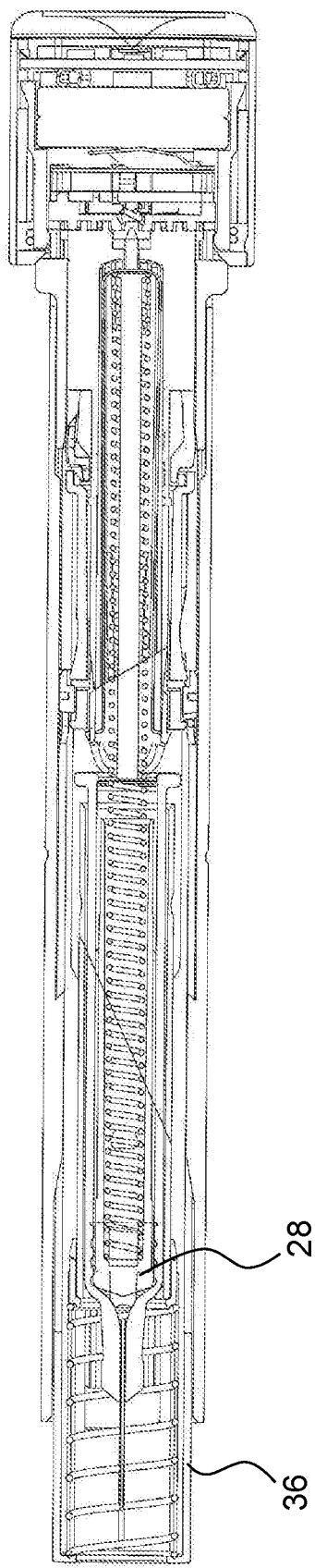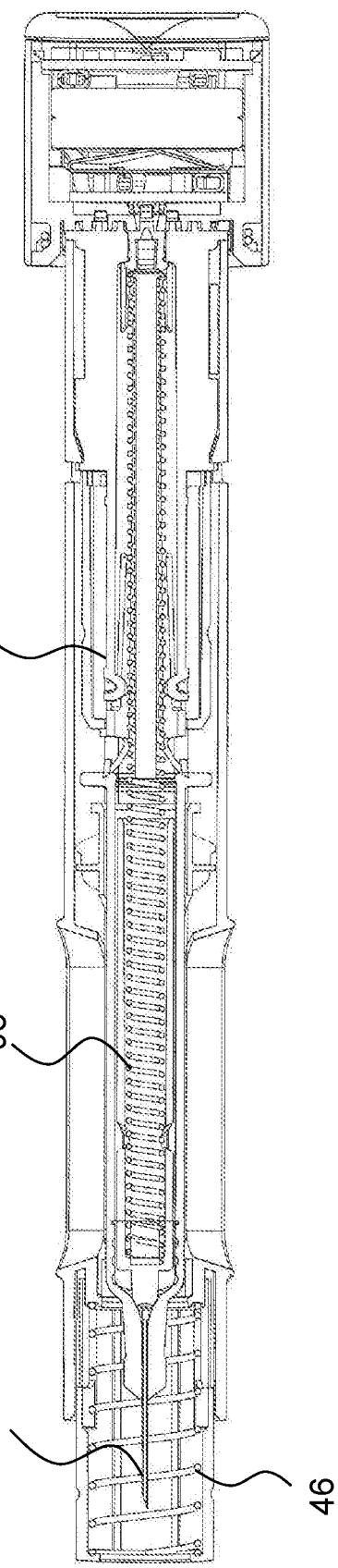

MONITORING UNIT

CROSS REFERENCE TO RELATED APPLICATIONS

The present application is a U.S. National Phase Application pursuant to 35 U.S.C. § 371 of International Application No. PCT/EP2017/055173 filed Mar. 6, 2017, which claims priority to European Patent Application No. 16161584.4 filed Mar. 22, 2016. The entire disclosure contents of these applications are herewith incorporated by reference into the present application.

TECHNICAL AREA

The present disclosure relates to a monitoring unit to be arranged and operated in connection with a medicament delivery device, which monitoring unit is to be removably attached to the medicament delivery device.

BACKGROUND

With the growing use of self-medication units that are handled by the patients themselves, there is an increased desire for providing information to care givers such as physicians and nurses who need to know how the patients' treatment schemes are followed. Thus, there is an increased desire for monitoring the progress of the schemes, and in that respect, a number of medicament delivery devices have been provided with additional functionality in order to both monitor the use of a medicament delivery device, to store data from the monitoring as well as communicating the stored data to external devices for further processing of the monitored data.

One example is disclosed in the document WO 2014/128156. It comprises a medicament delivery device arranged with a logging module that is capable of detecting movement of components inside the medicament delivery device. According to one embodiment the logging module is arranged with a rotary sensor capable of counting the number of steps that a dial ring member is rotated relative to the fixed housing, both when a dose is set and when a dose is expelled.

The obtained number of steps from the rotary sensor may be used for different information purposes. For instance, the time of setting and expelling a dose may be registered such that the time elapsed since the last dose was administered may be calculated. Also the dose size may be obtained from the rotary sensor. The obtained data may then be transmitted to an external device such as a smartphone or the like. The preferred means of communication between the module and the smart phone is via NFC technology.

A drawback of the solution described above is that the module is an integrated part of the medicament delivery device. Since such a module comprises a number of components, rendering it rather expensive to manufacture, it is only suitable for a medicament delivery device that can be used a large number of times with replaceable medicament containers, a so-called re-usable medicament delivery device. It is not suitable for disposable medicament delivery devices that are discarded after use.

Another solution is disclosed in document WO 2014/020008. It comprises a supplementary device that is intended to be connected to a medicament delivery device comprising a housing having a mating unit that is configured to tightly but releasably embrace the housing of the medicament delivery device. The supplementary device is arranged with optical and acoustical sensors for gathering information from the medicament delivery device. The supplementary device further comprises a user interface for information input as well as displaying information. The supplementary device is designed to monitor handling of the device, such as the setting of a dose and/or injection of a dose by acoustic sensors. The supplementary device may communicate with a blood glucose monitoring system via communication technology such as Bluetooth.

Even though the housing preferably is designed to tightly embrace the housing of a certain medicament delivery device, the connection is not unique and the supplementary device may be connected to a number of medicament delivery devices that have similar housing dimensions. There is thus a risk that a user may use the supplementary device on another medicament delivery device than the one intended. It is therefore possible that the information obtained by the supplementary device is corrupted and cannot be trusted.

It would be advantageous if the medicament delivery device could be arranged with monitoring units that are more versatile but yet provide accurate and correct data from a medicament delivery device intended to be used with the monitoring unit.

SUMMARY

In the present application, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

In the following description, the term "smart devices" will be used. In this context, smart devices may include electronic devices that are provided with processors that are capable of running computer programs, as well as comprising storage space to store programs and data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further, the smart devices may be provided with antennas for wireless communication with the networks. Also, the smart devices may be arranged with receiving and transmitting mechanisms capable of communicating with RFID/NFC tags, as well as programs capable of establishing and handling the communication with these tags. It is further to be understood that the smart devices may comprise near range communication technology such as RFID, NFC, Bluetooth, Ant, Zigbee, or the like.

The aim of the present disclosure is to remedy the drawbacks of the state of the art devices in this area of technology. This aim is solved by a monitoring unit comprising the features of the independent patent claim. Preferable embodiments form the subject of the dependent patent claims.

According to the present disclosure, it comprises a unit for monitoring a medicament delivery device, where the monitoring unit may comprise housing of suitable shape. For instance it may have a shape and dimensions complimentary to a housing of a medicament delivery device such as to form a unit with the medicament delivery device when attached. In this regard, the monitoring unit may be attachable to a distal end of the medicament delivery device.

The monitoring unit may preferably comprise a monitoring circuit arranged in the housing, capable of detecting and monitoring functions of the medicament delivery device. Functions that may be detected are numerous depending on the functionality of the medicament delivery device. Examples of functions comprise, the beginning and/or the end of a penetration sequence, the beginning and/or the end of an injection sequence, the extension of a medicament delivery member guard after completed injection and removal of the medicament delivery device, pressing of an activation element such as a button or a proximal end of a medicament delivery member guard.

The monitoring unit is preferably arranged with releasable holding elements. The releasable holding elements are designed to interact with a medicament delivery device for releasably holding the monitoring unit when attached to the medicament delivery device. In this regard, the monitoring unit is preferably arranged with locking elements that are designed to act on the attachment mechanism. Further, the monitoring circuit is arranged with at least one drive element operably connected to the locking elements such that activation of the monitoring unit will cause the locking elements to act on the releasable holding elements, preventing detachment of the monitoring unit from the medicament delivery device. This is a valuable feature since it is important that the monitoring unit is not removed during a dose delivery sequence, which may be the case if the user is not careful when handling the medicament delivery device.

According to a favourable solution, the monitoring circuit may be arranged with activation elements that are capable of activating the monitoring unit, where the activation elements may be arranged to interact with the medicament delivery device such that the monitoring unit is activated when attached to the medicament delivery device. This feature saves power of a power source in the monitoring unit because the monitoring unit is not active until it is attached. In this regard, the monitoring unit may be deactivated when removed from the medicament delivery device for saving power of the power source.

According to one feasible solution, the holding elements may be flexible in a generally radial direction and they are arranged to interact with mating holding elements on the medicament delivery device. This provides a removable attachment function where the flexibility provides a resilient holding force. In this regard, the flexible holding elements may comprise attachment tongues arranged with ledges, where the ledges are arranged to engage ledges of the mating holding elements of the medicament delivery device. Depending on the properties of the material and the dimensions of the tongues, the resilient holding force may be designed and adjusted such that good holding properties are obtained but also providing release forces that are not too high for e.g. users with poor dexterity and muscle force in their hands.

The monitoring unit may further comprise at least one drive element that is operably connected to the locking elements wherein, upon activation of the monitoring unit, the drive elements move the locking elements to a position blocking the flexible holding elements. According to one feasible solution, the locking element may be ring-shaped and is arranged movable in a longitudinal direction of the monitoring unit. With this solution the locking element is pushed along and radially outside the holding elements from a position where the holding elements may flex to a position preventing any flexing movement of the holding elements. In order to prevent the ring-shaped locking element from getting stuck before entering the locking position because of uneven force distribution from only one drive element, at least two drive elements may be arranged on opposite sides of the drive element.

Further, the drive element may be a linear actuator. Alternatively, the drive element may be a stepper motor having a cog wheel on its rotational shaft, acting on a toothed rack attached to the ring-shaped locking element and extending in the longitudinal direction of the monitoring unit. Other feasible solutions comprise miniature hydraulic or pneumatic actuators, electroactive polymers, piezoelectric actuators, thermal bimorph actuators, etc.

As an alternative, the locking element may be band-shaped and arranged with protrusions extending in the longitudinal direction arranged movable in a circumferential direction to a blocking position wherein the protrusions block the flexible holding elements. With this solution, instead of a linear movement of the locking element, it is rotated wherein the protrusions on the locking element may be moved from an initial position where the holding elements may flex in the radial direction to a locking position where the protrusions are positioned radially outside the holding elements, thereby preventing any flexing movement. With this solution, the drive element may be a stepper motor. On the other hand, all the above mentioned alternative drive elements may be utilized also for this solution.

As a further alternative, the locking element may be band-shaped and may be arranged with a through-going slit enabling radial expansion of the locking element during attachment, wherein the end surfaces of the slit are arranged with grip elements arranged to grip the drive element. With this third solution, the locking element is not moved by any drive element but is designed such as to be expandable in the radial direction by the slit, enabling flexing of the holding elements in the radial direction. The drive unit is in this case used for preventing radial expansion of the locking element after attachment.

According to one design, the slit is stepped, creating to oppositely directed tongues, which tongues are formed as hooks, through which a movable member of the at least one drive element can extend. With this design, the grip elements are created from the locking element itself. It is however to be understood that the grip elements may be formed in many other ways. For instance rings may be attached to the ends of the locking element adjacent the slit, through which the drive element may extend. Despite design however, an important factor is that the grip elements are aligned when the locking element is unaffected so that the drive element may pass through and lock the locking element. According to one solution, the drive element comprises a linear actuator. However, as with the first embodiment, other types of actuators may be utilized as described above.

The monitoring unit may further comprise a mechanical interface arranged to interact with a mating mechanical interface arranged on the medicament delivery device. In this respect, the mechanical interface may further comprise mechanical keying elements that are arranged with specific mechanical keying design. An activation switch may further be arranged on the mechanical interface, which will switch on the electronic circuit when the mechanical keying elements of the mechanical interface mate with a corresponding mechanical interface on the medicament delivery device having the corresponding mechanical keying design. If the two keying designs do not mate, the monitoring unit cannot be attached to the medicament delivery device and also, the monitoring unit is not activated. The mechanical keying elements may comprise protrusions and recesses arranged in predetermined patterns providing unique interfaces. In this respect, the activation switch may be positioned such in the interface that it is activated mechanically by said protrusions.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 2a shows a cross-sectional view of the medicament delivery device according to FIG. 1, FIG. 2b shows another cross-sectional view of the medicament delivery device according to FIG. 1, FIGS. 3-7 are detailed views of components comprised in the medicament delivery device according to FIG. 1, FIG. 11 shows an exploded view of the monitoring unit of FIG. 9, FIG. 12 shows an exploded view of the embodiment of FIG. 9, FIG. 15a shows a functional positions of the first embodiment, FIG. 15b shows another functional position of the first embodiment, FIG. 19a shows a cross-sectional view of the interaction between the monitoring unit and the medicament delivery device of FIG. 1, and FIG. 19b shows another cross-sectional view of the interaction between the monitoring unit and the medicament delivery device of FIG. 1.

DETAILED DESCRIPTION

Figure 3:
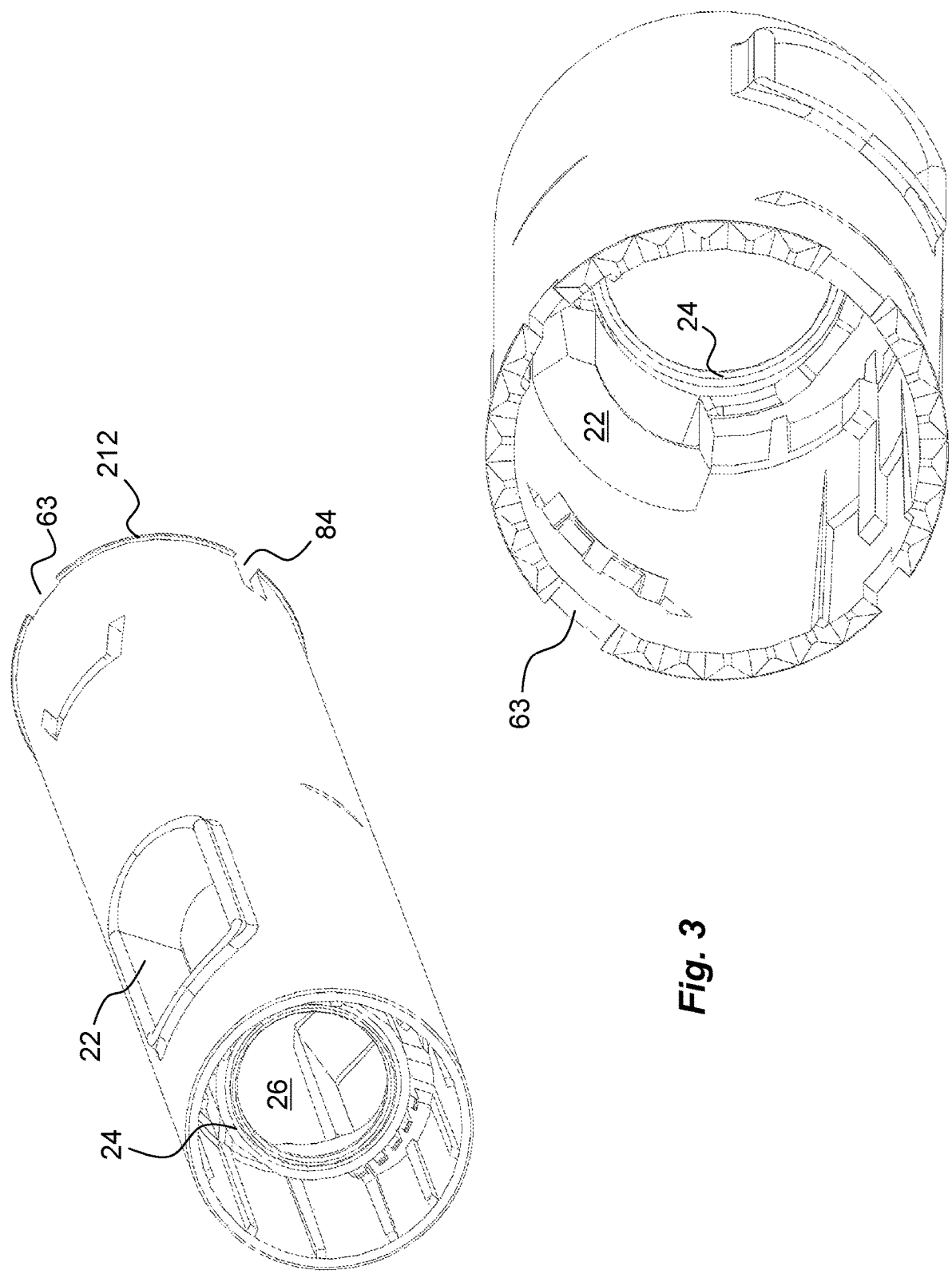

An example of a medicament delivery device that may be used with the present disclosure is shown in the drawings. It comprises a generally tubular elongated housing 10 having a distal end 12 and a proximal end 14, FIG. 1. The housing 10 is further arranged with openings or windows 16, through which a generally tubular medicament container 18 can be viewed. The medicament container 18 is placed in a medicament container holder 20. Each window 16 is further arranged with an inwardly directed ring-shaped circumferential ledge 22. As seen in FIG. 3, a support wall 24 is attached to the circumferential ledge 22, wherein the support wall 24 is arranged with a central passage 26. The edge of the central passage 26 as well as the inner edges of the circumferential ledges 22 of the windows 16 form support surfaces for the medicament container holder 20. The medicament container 18 is arranged with a movable stopper 28, FIG. 2. The medicament container 18 has a proximal end on which a medicament delivery member 30, is arranged, either made integral or connectable to the medicament container 18. The medicament delivery member 30 is preferably protected before use by a medicament delivery member shield 32 that in the embodiment shown is a so called rigid needle shield or RNS. It is however to be understood that other types of medicament delivery member shields may be used in order to obtain the desired protection of the medicament delivery member 30.

Figure 1:
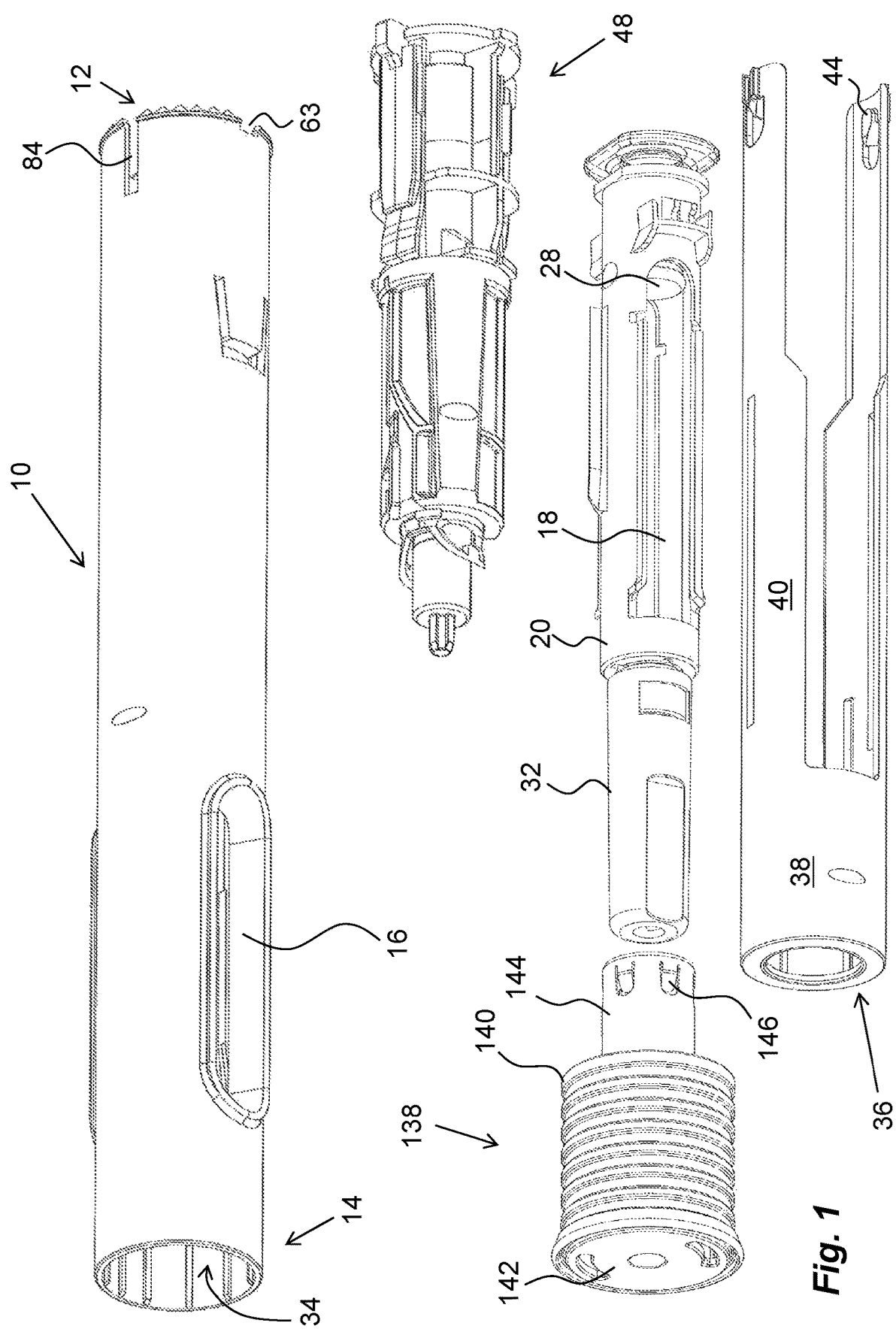
FIG. 1 is an exploded view of a medicament delivery device that may utilize a monitoring unit according to the present disclosure.

The proximal end of the housing 10 is arranged with a central passage 34, FIG. 1, through which a generally tubular medicament delivery member guard 36 extends, FIG. 1. The medicament delivery member guard 36 comprises a proximal tubular part 38 and two distally directed arms 40 extending from the tubular part 38. A medicament delivery member guard spring 42, FIG. 2a, is arranged between a distally directed circumferential wall part of the medicament delivery member guard 36 and a proximally directed surface of the support wall 24. The arms 40 are arranged slidable along the medicament container holder 20. At the distal end of the arms 40, inwardly directed protrusions 44 are arranged, FIG. 1. The protrusions 44 are arranged to operably interact with a tubular rotator 46, FIGS. 4 and 5, of a drive unit 48.

The rotator 46 has a generally tubular shape and is arranged with guide ridges 50 that are intended to cooperate with the protrusions 44 of the medicament delivery member guard 36 as will be described, wherein some sections 50, of the guide ridges are inclined in relation to the longitudinal axis L of the device. A proximal part of the rotator 46 is further arranged with proximally directed tongues 52 adjacent the guide ridges, wherein the free ends of the tongues 52 are arranged with wedge-shaped outwardly directed protrusions 54, the function of which will be described below. The rotator 46 is further arranged with ledges 55 on its inner surface at a distal end, FIG. 5, providing a space 57 between the ledges in a circumferential direction.

Figure 4:
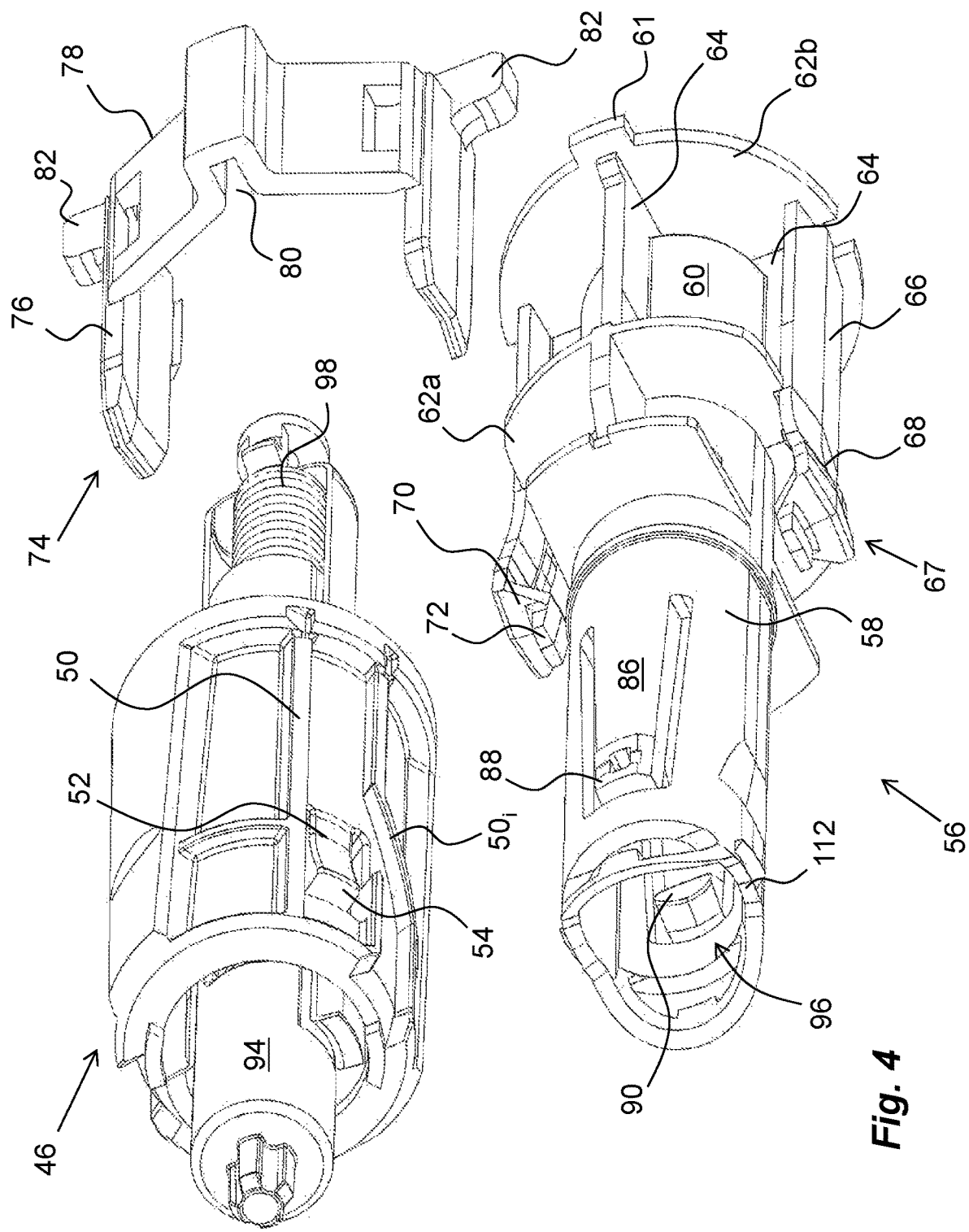

An actuator 56, FIG. 4, is further arranged operably to the rotator 46. It comprises a first proximal tubular section 58 having a diameter slightly smaller than the inner diameter of the rotator 46. It further comprises a generally tubular second section 60 arranged to fit into and to be attached to a distal part of the housing. The second section 60 is provided with two generally circular, radially extending, wall sections 62a, 62b. Four longitudinally extending wall sections 64 are arranged around the circumference of the second section 60 and extending between the radially extending wall sections 62a, 62b. The most distal of the wall sections 62b is arranged with radially outwardly directed protrusions 61 that fit into cut-outs 63, FIG. 1, on a distal edge of the housing of the medicament delivery device. On two oppositely positioned longitudinal wall sections 64 extending between the radial wall sections 62a, 62b, longitudinally extending ledges 66 are arranged. The ledges 66 extend in the proximal direction with holding elements 67 that in the embodiment shown comprises tongue-shaped flexible sections 68 having a somewhat outwardly inclined direction. The ends of the tongue-shaped sections 68 are each arranged with an inwardly directed section 70. On each inwardly directed section 70 a proximally directed ledge 72 is arranged, the function of which will be explained below. In an initial position of the holding elements 67 in relation to the rotator 46, the ledges 72 fit into the spaces 57 between the ledges 55 of the rotator 46, thereby providing a rotational lock of said rotator 46.

A release element 74, FIG. 4, is further arranged to the second section 60 of the actuator 56. The release element 74 comprises two elongated plate-like members 76 interconnected by a bridge 78. The bridge 78 has a central longitudinally extending groove 80 which fits onto one of the longitudinally extending wall sections 64 whereby the plate-like members 76 are positioned radially outside the ledges 66. The release element 74 is then slidable in the longitudinal direction such that the proximal ends of the plate-like members 76 can affect the proximally directed tongue-shaped sections 68 of the holding element 67 as will be described. The plate-like members 76 are further arranged with radially outwardly directed protrusions 82, which protrusions 82 are arranged to fit into slits 84 in the housing 10 at the distal end thereof, FIG. 1.

The first section 58 of the actuator 56 is further arranged with proximally extending arms 86 that are arranged flexible in a generally radial direction. The free ends of the arms 86 have outwardly extending protrusions 88 that are to interact with inner surfaces of the rotator 46 as will be described. Further the free ends of the arms 86 are arranged with inwardly extending protrusions 90, which protrusions 90 are intended to interact with recesses 92 on a generally elongated plunger rod 94, FIG. 6. The inwardly directed protrusions 90 extend into a central passage 96 of the actuator 56, in which passage 96 the plunger rod 94 fits.

The drive unit 48 further comprises a drive spring 98, FIG. 6, that in the embodiment shown is placed inside a cavity of the hollow plunger rod 94, wherein the drive spring 98 is positioned with a proximal end thereof in contact with an end wall 100 of the plunger rod 94, FIG. 2. Inside the drive spring 98, a guide rod 102 is arranged. The distal end of the drive spring 98 is in contact with a generally U-shaped element, hereafter named activator 104, having a base 106 and two arms 108, FIG. 6. The arms 108 of the activator 104 are directed in the proximal direction along, and in contact with, the outer surface of the plunger rod 94, wherein the free ends of the arms 108 are arranged with generally radially outwardly directed ledges 110. These ledges 110 are arranged to be in contact with a proximally directed surface 112, FIG. 4, surrounding the central passage 96 of the actuator 56.

Figure 8A:
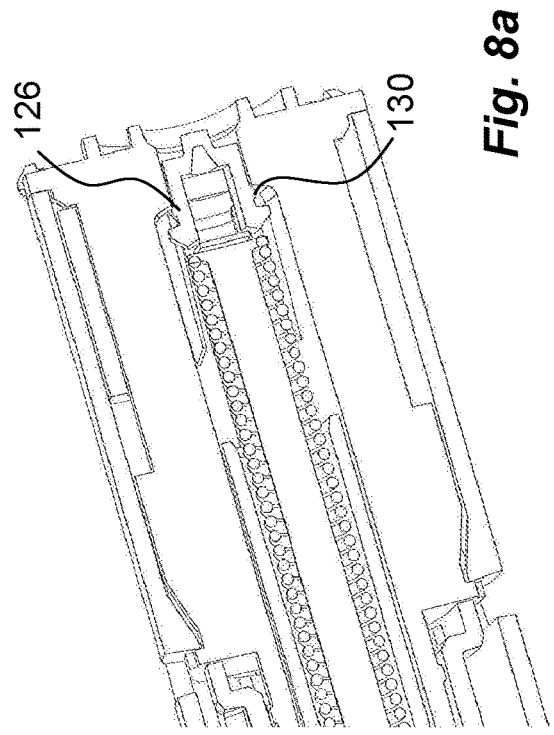
FIG. 8a is a detailed view of components comprised in the medicament delivery device according to FIG. 1.
Figure 8B:
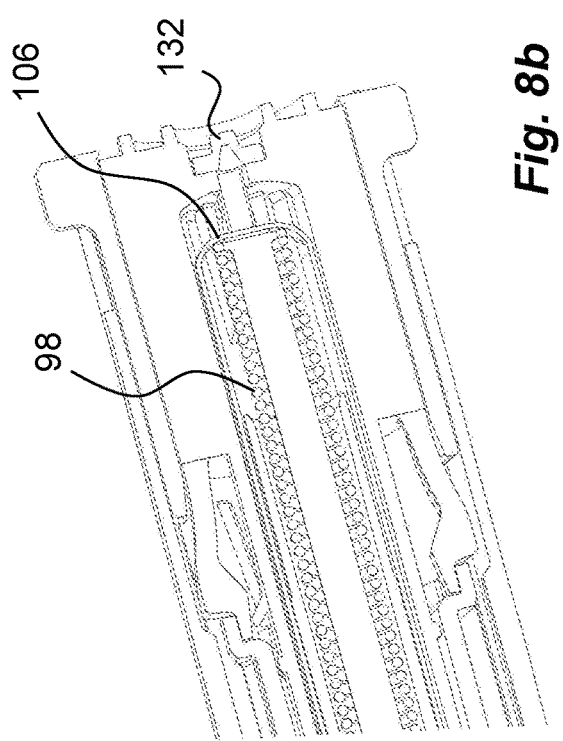
FIG. 8b is a detailed view of components comprised in the medicament delivery device according to FIG. 1.

The activator 104 further comprises an activator element 114, FIGS. 6 and 7, arranged in a distal end wall 116 of the housing 10 of the medicament delivery device. In the embodiment shown, the distal end wall comprises the most distal of the wall sections of the actuator. In the embodiment shown the activator element 114 has a generally disk-shaped body 118 arranged to fit into a cylindrical, central passage 120 in the end wall 116. The central passage 120 is arranged with a wall section 122 having a generally rectangular opening 124. The proximally directed surface of the disk-shaped body 118 is arranged with two proximally directed tongues 126 that are somewhat flexible in the radial direction. The tongues 126 are arranged to extend through the rectangular opening 124. The free ends of the tongues 126 are arranged with outwardly directed ledges 128. Further, the outer surfaces of the tongues 126 are arranged with transversal ridges 130. In an initial position, the ridges 130 are adjacent the inner edge of the central passage 120 and the proximal ends of the tongues are in contact with the base 106 of the activator 104, as seen in FIG. 8a. The distally directed surface of the disk-shaped body 118 is arranged with a central protrusion 132. Further, the distally directed surface of the end wall 116 is arranged with a number of concentric rings 134 and grooves 136 as seen in FIG. 7.

The medicament delivery device is further arranged with a medicament delivery member shield remover 138, FIG. 1. It comprises a generally tubular grip part 140 having an end wall 142. The distally directed surface of the end wall 142 is arranged with a seat in which a generally tubular grip element 144 is placed. The grip element 144 will be coaxial with and surrounding the medicament delivery member shield 32 when the medicament delivery member shield remover 138 is attached to the proximal end of the medicament delivery device. The grip element 144 comprises a number of generally proximally directed somewhat inwardly inclined tongues 146 that are engaging the outer surface of the medicament delivery member shield 32.

Figure 9:
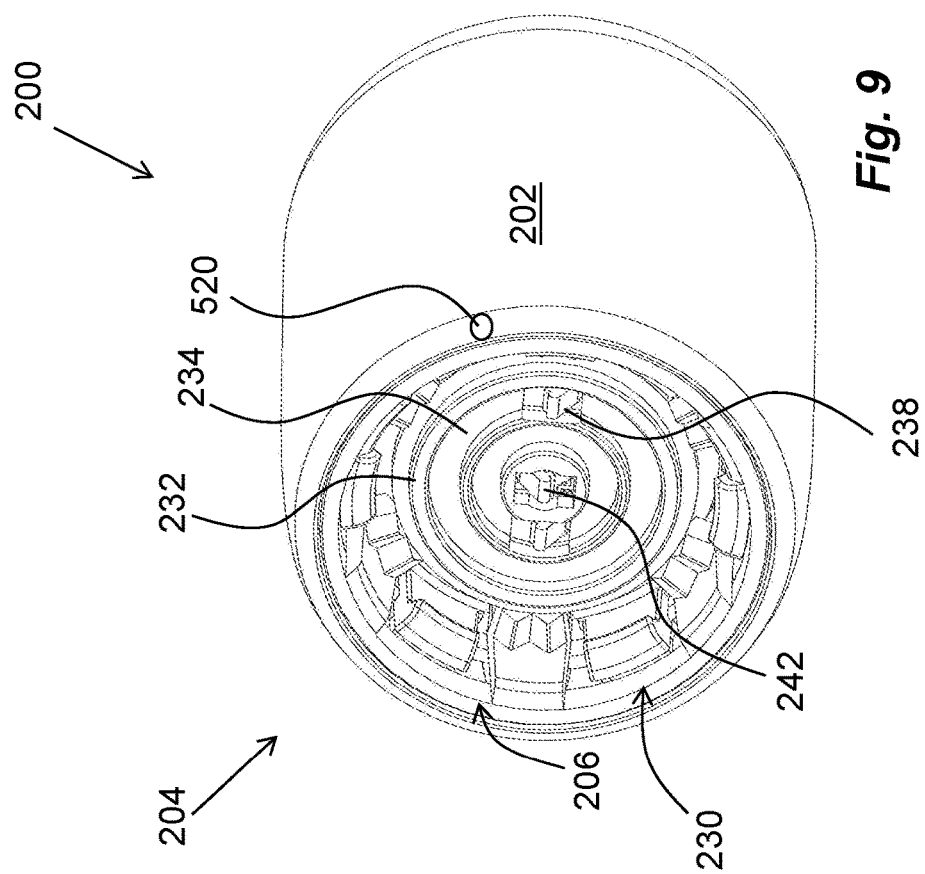
FIG. 9 shows an embodiment of a monitoring unit according to the present disclosure.

According to the present disclosure, a monitoring unit 200, FIGS. 9 and 11, is arranged to be operably connected to a medicament delivery device such as described above. The monitoring unit 200 comprises a housing 202 that could have a corresponding shape and appearance as the medicament delivery device that it is to be connected to, even though that is no prerequisite. The housing 202 has a proximally directed attachment mechanism 204, FIG. 10 a and b, that is designed to interact with a distal end of the medicament delivery device. In the embodiment shown, the attachment mechanism 204 comprises a central passage 206 which has a shape and dimension so as to fit onto the distal end of the medicament delivery device.

Figure 10B:
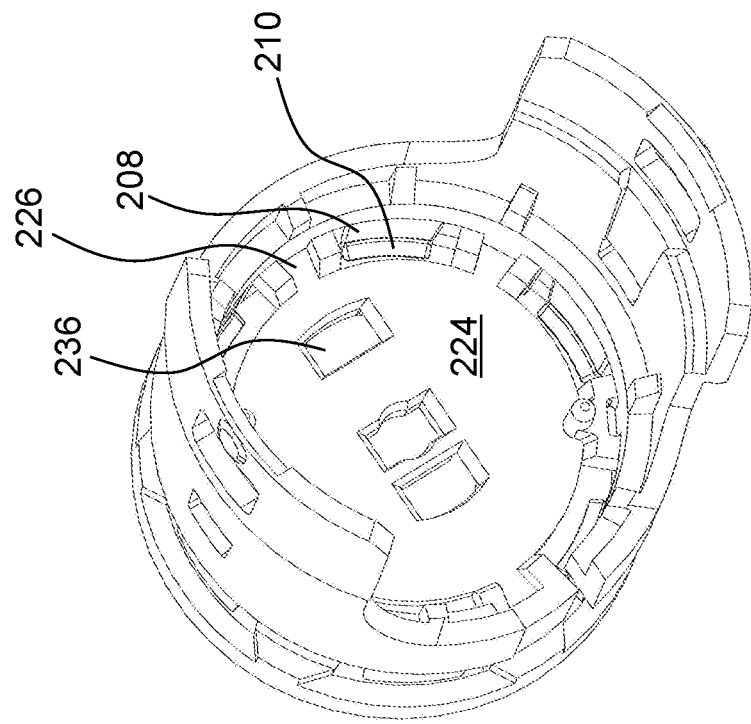
FIG. 10b shows a detailed view of components comprised in the monitoring unit of FIG. 9.
Figure 10A:
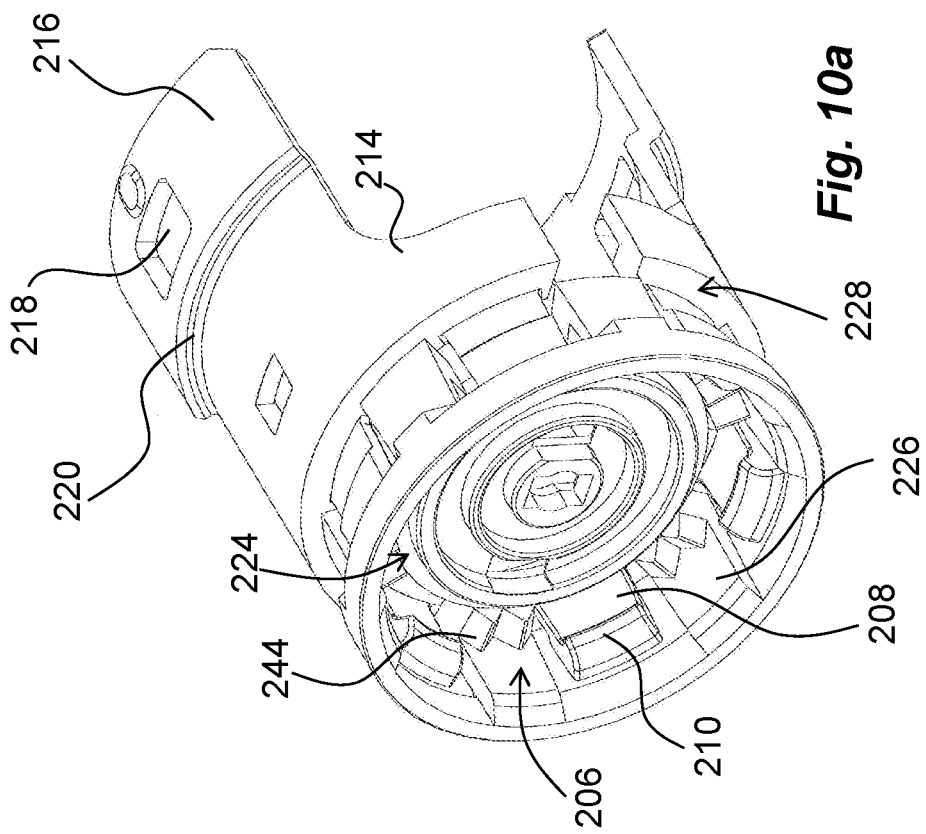
FIG. 10a shows a detailed view of components comprised in the monitoring unit of FIG. 9.

In order for the connection to be releasable, the attachment end of the monitoring unit 200 is arranged with an attachment mechanism that comprises holding elements in the form of a number of attachment tongues 208, FIG. 10, that are flexible in the generally radial direction. The free ends of the attachment tongues 208 are arranged with inwardly directed ledges 210 that are to cooperate with corresponding holding elements in the form of an annular ledge 212, FIG. 7, at the distal end of the housing of the medicament delivery device. The attachment tongues 208 are attached to a generally tubular body 214, which tubular body 214 is arranged with two oppositely positioned, distally directed, tongues 216. The free ends of the tongues 216 are arranged with cut-outs 218 and proximally directed ledges 220, which ledges are arranged to cooperated with distally directed end surfaces of longitudinally extending ribs 222, on an inner surface of the housing 202, FIG. 11. Body 214 is further arranged with a plate-shaped contact element 224 at its proximal end, FIG. 10b, where the contact element 224 is attached to the body a number of bridges 226. The bridges 226 are placed somewhat radially inwards in relation to the outer surface of the body 214 such that an annular groove 228 is formed. Further, in the spaces between the bridges 226 the free ends of the attachment tongues 208 are placed. The attachment tongues 208 and the bridges 226 are designed and positioned such that the outer surfaces of the attachment tongues 208 are placed somewhat radially outside the bridges 226.

A mechanical interface 230 is arranged on the monitoring unit 200, FIG. 9. The mechanical interface 230 may comprise a number of rings 232 and grooves 234 on the proximally directed surface of the contact element 224 having a design that fits together with the rings 134 and grooves 136 of the end surface of the medicament delivery device, forming a contact interface. Further, the contact element is preferably arranged with a number of passages 236, in which passages 236 switches 238 are placed. The switches are operably connected to electrical switching elements 240, FIG. 12, that will enable activation of the monitoring unit as will be described. Preferably the switches 238 are arranged and designed to interact with contact surfaces on the medicament delivery device such that the switches are activated when the monitoring unit is attached to the medicament delivery device. Preferably the positions of the switches 238 of the electrical switching elements are arranged in a certain pattern that can be specific for a certain monitoring unit and wherein a certain medicament delivery device is arranged with contact surfaces that have the same design so that all switches are activated when the monitoring unit is attached to the medicament delivery device. In this manner, there is a further keying requirement that needs to be fulfilled in order to activate the monitoring unit. For example the contact surfaces are the rings and grooves wherein the switches are positioned at different distances in a radial direction as seen in FIG. 9. The advantage with having rings is that the angular position between the monitoring unit and the medicament delivery device is not important when the two are interconnected. Further, as seen in FIG. 9, since the switches 238 are placed in the grooves 234, manipulation of the switches 238 by fingers is difficult, providing increased security against improper use of the monitoring unit 200.

Further, in order to activate the monitoring unit at a certain point of operation of the medicament delivery device, such as for instance at the end of a dose delivery sequence, the monitoring unit may be provided with an activation switch 242. In the embodiment shown in FIG. 9, this activation switch 242 may be placed in a central position of the interface of the monitoring unit. The activator of the medicament delivery device is then used for activating the monitoring unit as will be described.

The interface between the medicament delivery device and the monitoring unit could further comprise mechanical patterns that are to interact with each other. For instance the proximal surface of the contact element 224 could comprise a number of teeth 244 for example around a circumference. These teeth 244 are arranged to cooperate with corresponding teeth 246, FIG. 7, on the distal end of the medicament delivery device, wherein the number of teeth, the design of the teeth and the positions of the teeth are chosen such that a keying function is obtained. Thus, only monitoring units 200 and medicament delivery devices that have the same pattern can be inter-connected. This provides the possibility of customizing the monitoring unit 200 with the medicament delivery device such that only certain connections are possible.

Even though the mechanical interface has been described with annularly arranged teeth and ring-shaped protrusions and ring-shaped grooves, the skilled person can easily design other mechanical configurations that provide a unique keying function.

The monitoring unit 200 is arranged with a number of functions and features that may be activated when the activation switch 242 is operated as described above. One basic feature is a monitoring circuit 398 that comprises an electronic circuit 400 that in the embodiment shown is divided onto two generally disk-shaped printed circuit boards. The electronic circuit 400 comprises a processor 402, FIG. 10, capable of processing data program code for performing different tasks. The data program code is preferably stored in appropriate memory elements 404, in which also retrieved data may be stored, as will be described. The monitoring circuit 398 is further arranged with some power supply 406 such as button cells, photovoltaic panels, etc. Further, the above mentioned switching elements 240, 242 are electronically connected to the electronic circuit 400. In this respect it might be that all switches need to be operated at the same time in order for the monitoring unit to be activated. The electronic circuit 400 may further be arranged with a user communication circuit 408 that is arranged and programmed to communicate with a user. The user communication circuit 408 may comprise display elements that can communicate visually, e.g. by text stored in the electronics module that is displayed on a suitable display 410 on the monitoring unit, for instance at the distal end where it is clearly visible for a user. In addition to, or instead, the user communication circuit may comprise audio elements 412 that can communicate audibly, e.g. by a recorded message stored in the electronics module that is played in an appropriate loudspeaker of the electronics module or of the device as such.

A further development of the activation function is to provide the monitoring unit 200 with at least one communication circuit 414. The communication technologies that the communication circuit 414 may utilize may comprise near range communication technology such as RFID, NFC or the like, as well as Bluetooth, Ant, ZigBee, just to mention a few. This type of wireless communication technology may also be used to activate the monitoring unit. The communication circuit may be used for monitoring the usage of the medicament delivery device such that information is transmitted from the medicament delivery device to the monitoring unit.

According to a possible feature, if the monitoring unit 200 is provided with communication circuits, then monitored data obtained by the monitoring unit may be transferred to external storage sources and/or external devices. If for instance NFC technology is used, then a mobile NFC-enabled device may derive the monitored data from the usage management module. The same functionality may also be provided when using Bluetooth communication technologies.

The mobile device may then either be capable of processing the data, such as e.g. calculating the time and date of an occurrence of the medicament delivery device, or may in turn transmit the monitored data to external databases via the communication technologies of the mobile device, such as cellular radio communication networks, e.g. GSM, 3G, 4G, etc. and/or wireless local area networks, which networks can provide access to the internet and thus to a large number of external data storage sources, data handling centres, etc.

Regarding communication technologies, it is of course possible to incorporate the above mentioned communication technologies in the monitoring unit 200 as such. Then the monitoring unit may communicate directly with external data storage sources, data handling centres etc. via the communication networks. The monitored data may preferably be accessible to a physician or the like skilled person that is responsible for the treatment of the user of the medicament delivery device and who might have put together a treatment scheme. This retrieved monitored data may then be evaluated to derive information such as adherence, and the lack of which may lead to measures from the physician.

The electronic circuit 400 may further be arranged with a positioning circuit 416 whereby the geographical position of the user may be obtained and used for different purposes. In this respect, the positioning may be obtained by different functions. Either the electronics circuit is provided with a GPS-module, whereby the actual position of the user when the dose is delivered is recorded by GPS coordinates. Another possibility is to use the GSM-function for locating the position. The GPS-function and the GSM-function may further be combined with a WIFI location function for improved indoors location.

Regarding the activation of the monitoring unit, the electronic circuit could preferably be arranged with a suitable switch-off functionality, such as a timer function that will switch off the power to the circuitry after a certain period of time, for instance after completed medicament delivery operation. This will prolong the life of the power source in that it is not active when no action is taking place. Further, the electronic circuit may be arranged with a delay function that for example delays the sending of certain information. This may be used if the monitoring unit is activated during a dose delivery sequence but not at the end. The signal that the dose has been delivered can then be delayed so that it is ascertained that the whole dose has been delivered. The signal may for example be an audible signal from the monitoring unit to be heard by the user. With this delaying function, the point of activation of the monitoring unit is not so critical.

Since the monitoring unit is detachable from the medicament delivery device, it may be used together with disposable medicament delivery devices as well as re-usable medicament delivery devices and since it may be used many times with many devices and/or many dose delivery operations, it does not increase the total cost of a medicament treatment scheme in any major way.

Further, even though the activation of the monitoring unit has been described in relation to an end of dose operation, it is to be understood that the monitoring unit may be activated by a number of different features, functions and operations such as e.g. removal of protective caps, penetration of an injection needle, start and/or end of a dose delivery sequence, shielding of an injection needle after withdrawal. The skilled person working with design of medicament delivery devices has no difficulties in identifying suitable occurrences during the operation of a medicament delivery device when an activation feature may be added.

The monitoring unit is further arranged with a locking mechanism. It comprises a locking element 500 that in the embodiment shown in FIGS. 11, 12 and 15 is arranged as a ring 500 which is to be positioned in the groove 228. As seen in FIG. 15 the width of the ring in the longitudinal direction is smaller than the width of the groove 228. The electronic circuit 400 is arranged with a number of drive elements 502, FIGS. 11, 12, capable of providing linear movement in the longitudinal direction of the medicament delivery device. The drive elements 502 may for example be linear actuators that often comprise shafts 504 that may be moved linearly in relation to a housing 506. The shaft 504 is connected to the ring 500 so that when the drive element or elements 502 are activated, the ring 500 is moved in the longitudinal direction in the groove. Only one drive element is shown in the drawings, but in order to obtain a more even distribution of the load, not causing a tilting of the ring during movement, at least two drive elements should preferably be arranged, then preferably placed on opposite sides of the monitoring unit.

Figure 13:
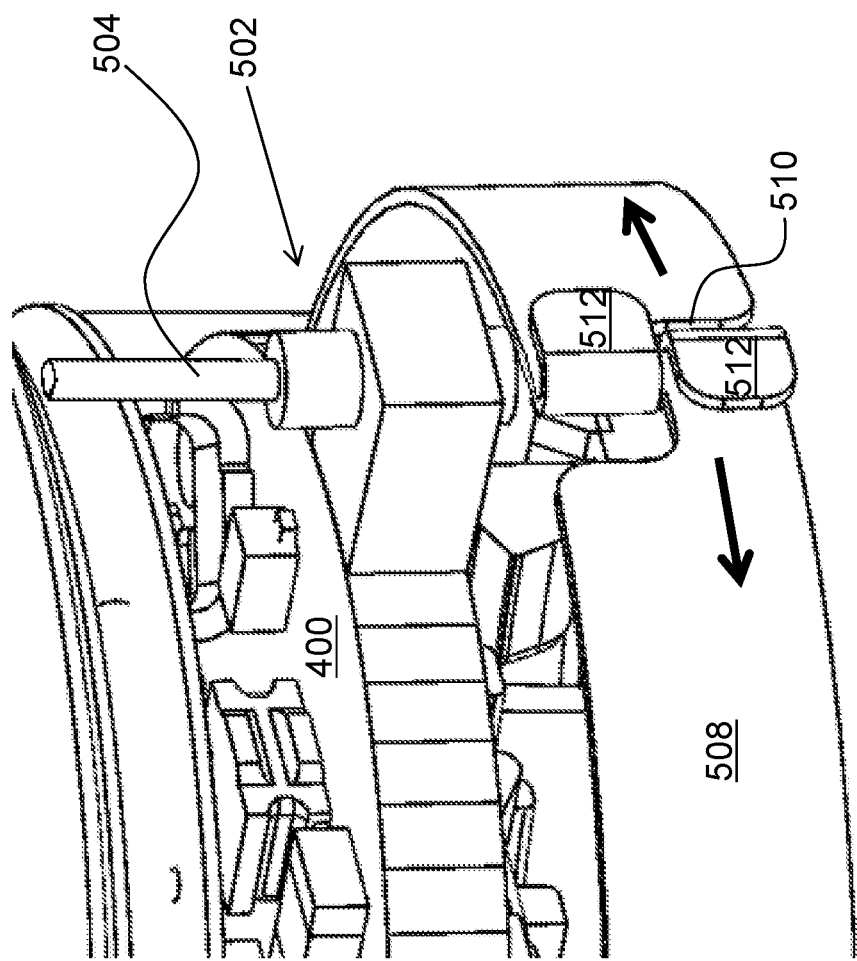
FIG. 13 shows a second embodiment of a monitoring unit according to the present disclosure.

FIG. 13 shows a second embodiment of a locking mechanism utilizing a linear actuator as a drive element 502. However, instead of moving a ring-shaped locking element, the locking element of the second embodiment is arranged as a wide band-shaped ring element 508 made of an elastically deformable material and provided with a stepped transversal slit 510, creating two oppositely directed tongues. The tongues are bent 180 degrees to form hook-shaped grip elements 512 positioned in line with each other along a longitudinal direction as seen in FIG. 13. The curvature of the grip elements 512 are such as to correspond generally to the circumference of the shaft 504 of the drive element 502.

Figure 14:
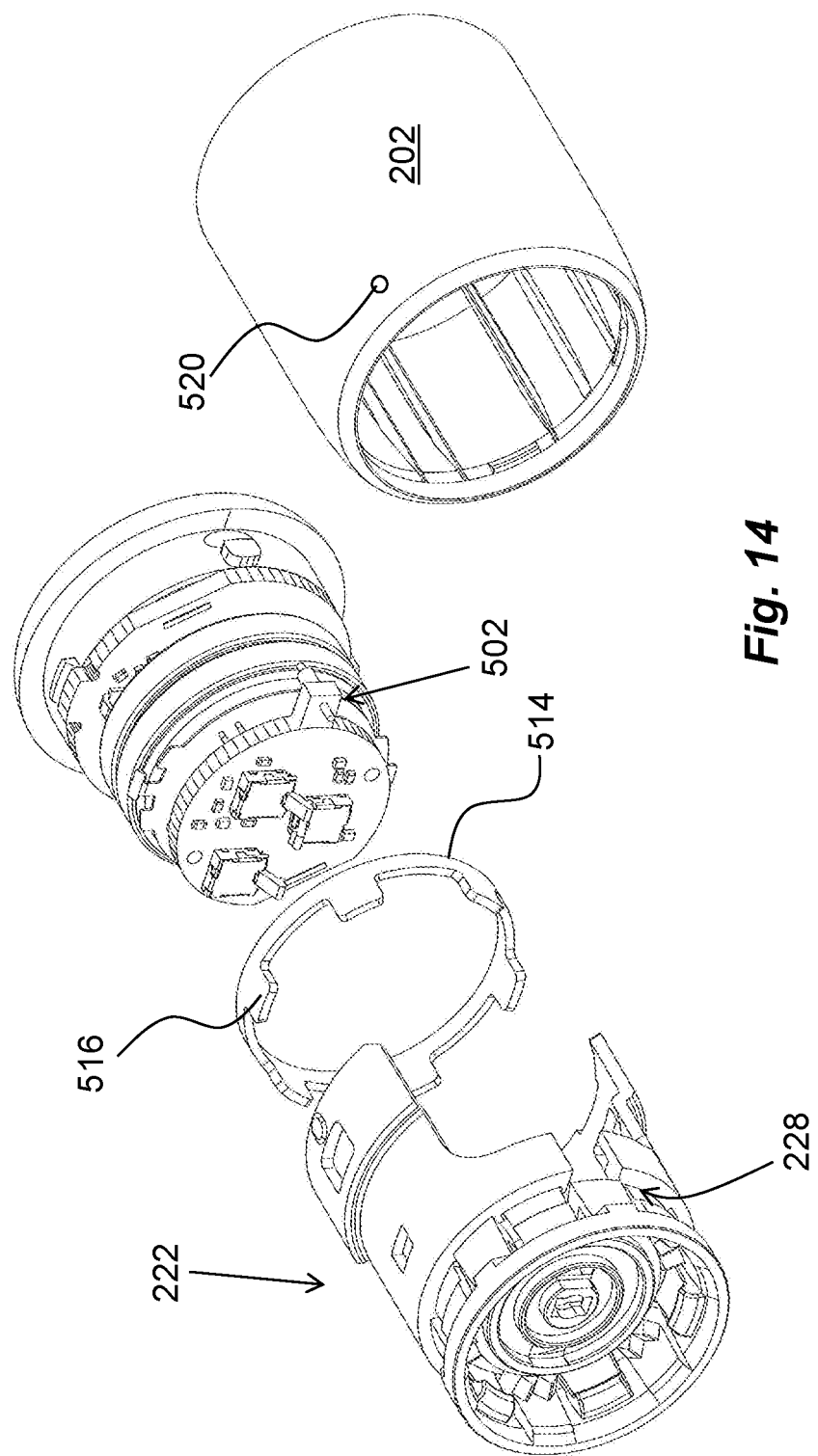
FIG. 14 shows a third embodiment of a monitoring unit according to the present disclosure.
Figure 16:
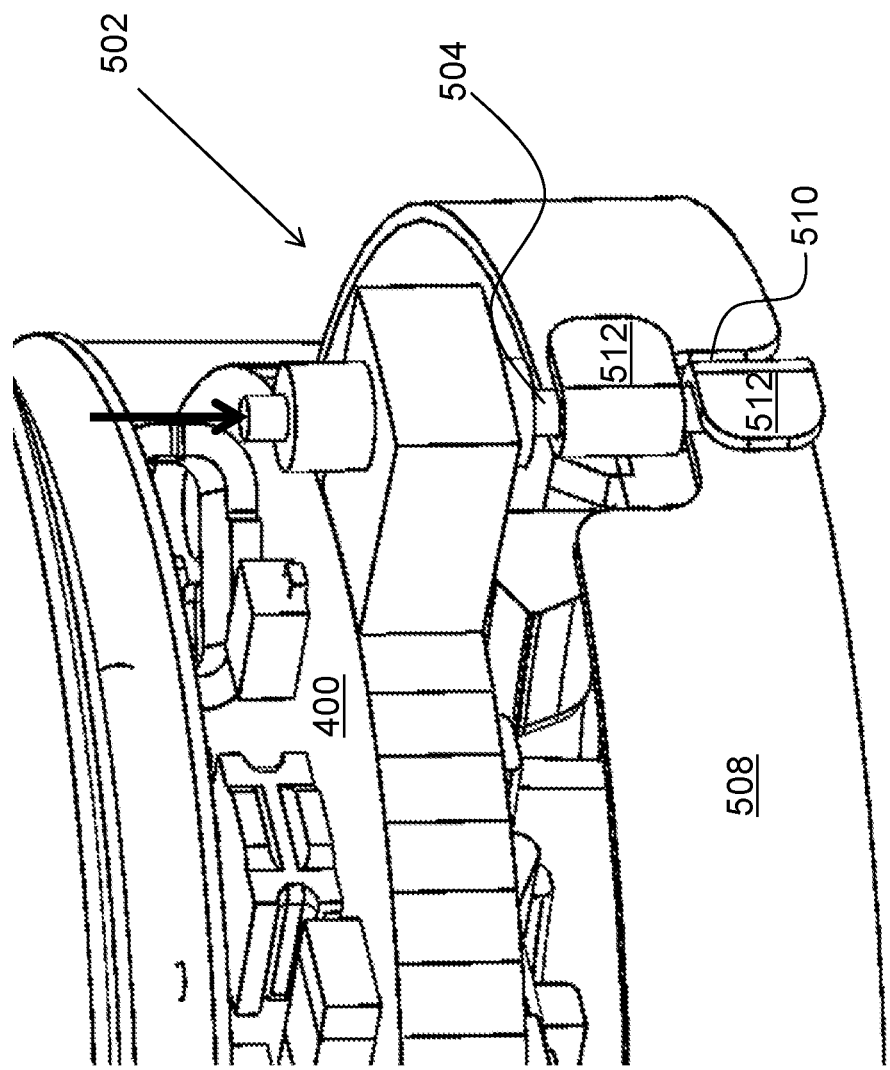
FIG. 16 shows a functional position of the second embodiment.

A third embodiment is shown in the FIG. 14. Here a locking element 514 is band-shaped and provided with a number of tongues 516 extending from its proximal edge. At least one drive element 502 is arranged in contact with the locking element as seen in FIG. 16. In this embodiment, the drive element may be a stepper motor having a rotational shaft 504 in contact with an outer surface of the locking element 514. The contact surfaces between the shaft 504 and the locking element 514 may comprise frictional features or form-fitting features such as a small cogwheel on the shaft cooperating with a toothed rack on the locking element. It is however to be understood that other types of rotation transferring elements may be utilized in order to obtain the desired function. When the drive element is activated, it will turn the locking element in the groove around the longitudinal axis.

The device is intended to function as follows. When the medicament delivery device is delivered to a user, a medicament container 18 with an attached medicament delivery member shield 32 has been placed in the medicament container holder 20 and a medicament delivery member shield remover 138 has been attached to the proximal end of the medicament delivery device. The drive spring 98 has been tensioned by pushing the plunger rod 94 distally relative to the actuator 56 such that the inwardly directed protrusions 90 of the arms 86 of the actuator 56 engage the recesses 92 of the plunger rod 94, thereby holding the spring-biased plunger rod 94.

When a medicament delivery device is to be used, a monitoring unit 200 has to be attached. The monitoring unit is thereby pushed onto the distal end of the medicament delivery device, whereby a proximal surface of the monitoring unit comes in contact with a distal surface of the protrusions 82 of the release element 74. Further pushing of the monitoring unit 200 in relation to the medicament delivery device will cause the release element 74 with its plate-like members 76 to be moved in the proximal direction. The proximal ends of the plate-like members 76 then act on the tongue-shaped sections 68 such that the tongue-shaped sections 68 are moved radially inwards whereby the ledges 72 are moved out of engagement with the space 55 of the rotator 46, whereby the rotator 46 is free to rotate as will be described. Further, the inwardly directed ledges 210 of the tongues 208 of the monitoring unit 200 will come in contact with the distal edge of the medicament delivery device and will flex outwardly in the radial direction, whereby the ledges 210 pass the edge. The tongues will then grip the annular ledge 212, attaching the monitoring unit to the medicament delivery device. The interfaces of the two are keyed to each other if the proper monitoring unit is used to the intended medicament delivery device. Some of the switches are then activated by the interface, making the monitoring unit ready for activation and for performing functions as will be described below.

When looking at the first embodiment, during attachment of the monitoring unit, the ring 500 is in its most distal position in the groove 228, FIG. 15a, allowing the tongues to flex radially as described above. When now the monitoring unit 200 is attached, the activation of the switches will in turn activate the monitoring unit 200 such that the drive elements 502 will be operated. According to the first embodiment, the at least one drive element 502 is activated whereby its shaft 504 is moved in the proximal direction. This in turn will cause the ring 500 to be moved in the proximal direction, FIG. 15b, whereby it will be positioned radially outside the attachment tongues 208, thereby preventing any flexing action in the radial direction, which in turn locks the monitoring unit 200 to the medicament delivery device. Thus when the monitoring unit 200 is activated, it cannot be removed from the medicament delivery device.

When looking at the second embodiment shown in FIGS. 13 and 16, when the monitoring unit 200 is not activated the shaft 504 is out of contact with the grip elements and when the monitoring unit is attached to the medicament delivery device, the tongues may flex radially outwardly as described above, against a force created by the elastic expansion in the radial direction of the band-shaped locking element 508 due to the slit 510. When the monitoring unit 200 is attached to the medicament delivery device, the locking element 508 resumes its initial position with the grip elements 512 aligned in relation to the shaft of the drive element such that when the drive element 502 is now activated, the shaft 504 enters the grip elements 512 as seen in FIG. 16, thereby preventing any expansion of the locking element 508 and thus locking the monitoring unit to the medicament delivery device.

Figure 17B:
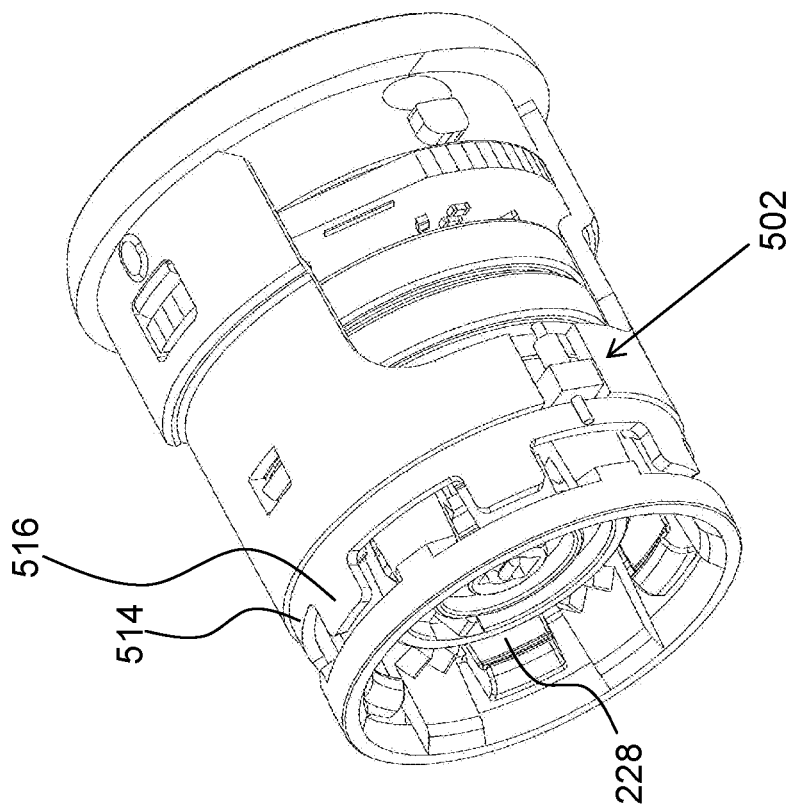
FIG. 17b shows another functional position of the third embodiment.
Figure 17A:
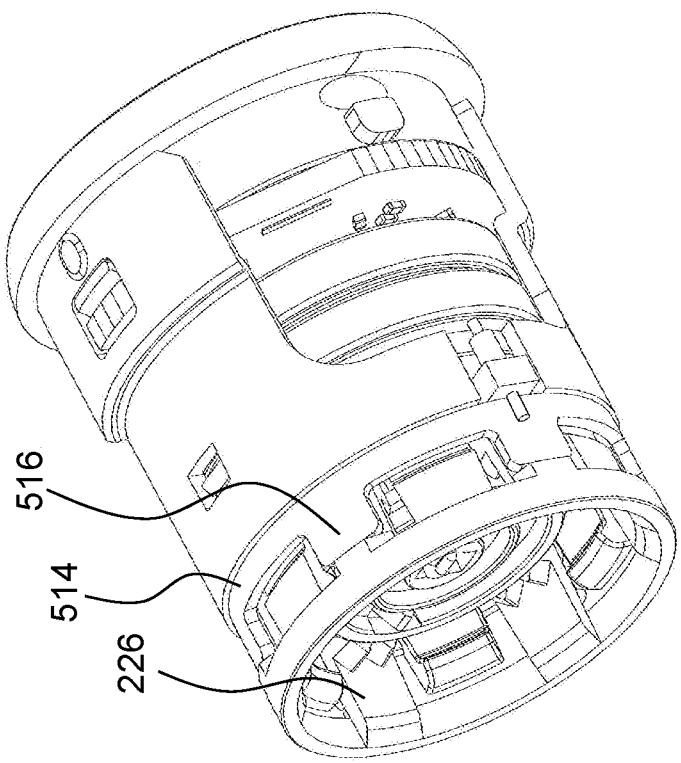
FIG. 17a shows a functional positions of the third embodiment.

When looking at the third embodiment shown in FIGS. 14 and 17, when the monitoring unit 200 is not activated, the band-shaped locking element 514 is rotationally positioned such that the proximally directed protrusions 516 are positioned radially outside the bridges 226, FIG. 17a, whereby the tongues 228 are free to flex in the radial direction as described above, allowing an attachment of the monitoring unit to the medicament delivery device as described above. When then the monitoring unit is connected the drive element 502 is activated, wherein the stepper motor rotates its shaft. This will in turn cause the locking element 514 to rotate around the longitudinal direction whereby the tongues 516 will be positioned radially outside the tongues 228, preventing them from flexing in the radial direction. The monitoring unit is thus locked to the medicament delivery device.

When a dose of medicament is to be delivered, the medicament delivery member shield remover 138 is removed from the proximal end of the medicament delivery device by pulling it in the proximal direction. Because of the engagement of the tongues 146 with the medicament delivery member shield 32, the medicament delivery member shield 32 will also be pulled in the proximal direction, removed from the medicament delivery member 30. The proximal end of the medicament delivery device is then pressed against a dose delivery site. This causes the medicament delivery member guard 36 to move inside and relative the housing 10. This in turn causes the protrusions 44 of the medicament delivery member guard 36 to move along the guide ridges 50 of the rotator 38 such that the protrusions will come in contact with the inclined guide ridge 50,, which will cause the rotator 46 to turn around the longitudinal axis L of the device i.e. to rotate.

Thus, as described above, if the monitoring unit 200 has not been previously attached, the rotator will be prevented from rotating by the ledges 72 in the spaces 57 and, consequently, it will be impossible to use the device.

Figure 18A:
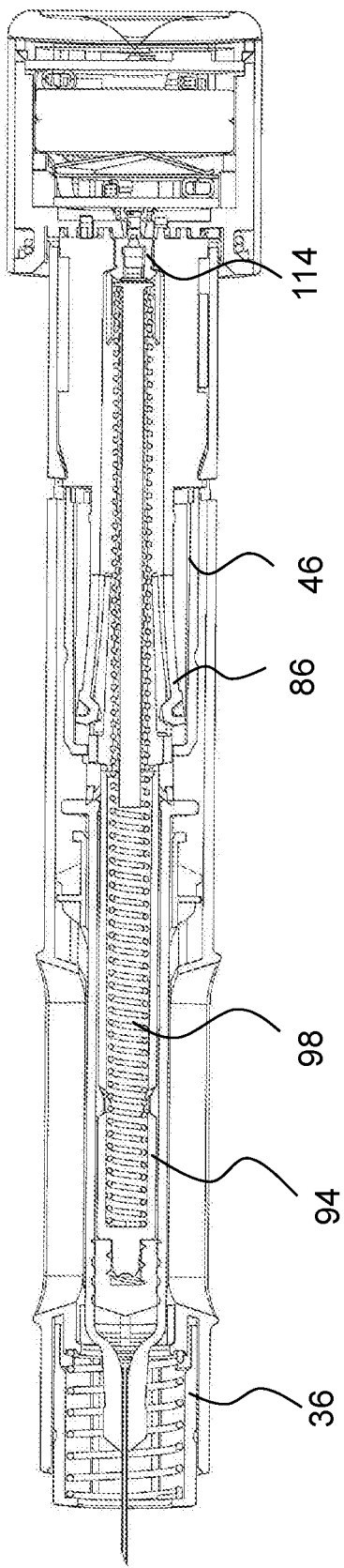
FIG. 18a shows a cross-sectional view of the interaction between the monitoring unit and the medicament delivery device of FIG. 1.

The turning/rotation of the rotator 46 will cause the outwardly directed protrusions 88 of the actuator 56 to be moved out of contact with inner surfaces of the rotator 46. The arms 86 of the actuator 56 are now free to flex outwardly, whereby the inwardly directed protrusions 90 of the arms 86 are moved out of contact with the recesses 92 of the plunger rod 94, FIG. 18a.

Figure 18B:
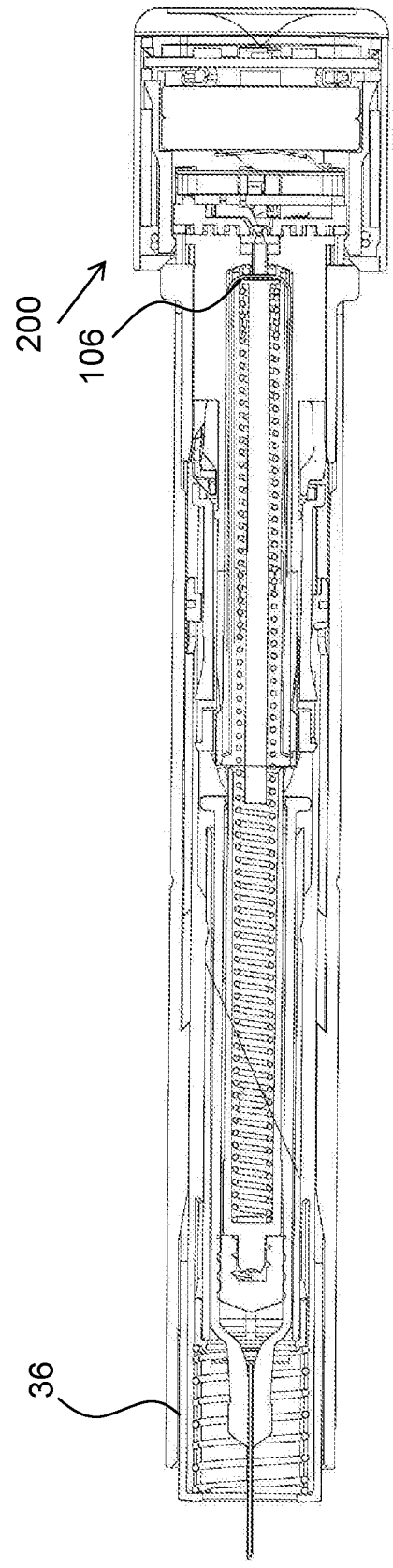
FIG. 18b shows another cross-sectional view of the interaction between the monitoring unit and the medicament delivery device of FIG. 1.

The plunger rod 94 is now free to move in the proximal direction due to the force of the drive spring 98, wherein the proximal end of the plunger rod 94 acts on, and moves, the stopper 28 inside the medicament container 18 in the proximal direction such that a dose of medicament is expelled through the medicament delivery member 30, FIG. 18.

When the stopper 28 has been moved by the plunger rod 94 to almost the proximal end inside the medicament container 18, the plunger rod 94 is moved out of contact with the arms 108 of the activator 104. The arms 108 of the activator 104 are thus free to flex inwards such that the ledges 110 are moved out of contact with the proximally directed surfaces 112 of the actuator 56, and due to the force of the drive spring 98 in contact with and acting on the base 106 of the activator 104, the activator 104 will be moved in the distal direction. Because of the contact with the activator element 114, the activator element 114 will also be moved distally in the central passage 120 such that the central protrusion 132 will extend out of the central passage 120 and affect the activation switch 242 of the monitoring unit, FIG. 18, whereby the monitoring unit 200 is activated as described above. The movement of the activator element 114 is stopped when the outwardly directed ledges 128 hit a proximally directed surface of the end wall 116 of the medicament delivery device. This sudden stop will also provide an audible and tactile signal that the dose delivery sequence is completed and that it is safe to remove the medicament delivery device.

When the dose has been delivered the medicament delivery device is removed from the site. This in turn will cause the medicament delivery member guard 36 to be moved in the proximal direction by the medicament delivery member shield spring 42, to extend through the proximal end of the medicament delivery device and to cover the medicament delivery member 30. Since the rotator 46 has been rotated, the protrusions 44 of the medicament delivery member guard 36 will slide over the wedge-shaped protrusions 54 of the tongues 52 of the rotator 46 and be placed proximally thereof, thereby locking the medicament delivery member guard 36 in the extended, covering position, FIG. 19.

The monitoring unit 200 may now be removed from the medicament delivery device before discarding the medicament delivery device. One feasible solution is that the locking mechanism again activated for instance a certain time after the activation switch of the monitoring unit has been operated at the end of a dose delivery sequence, whereby the locking element is removed from the flexible tongues. The removal of the monitoring unit may be indicated or communicated to a user via the communication circuit 408, e.g. providing visual, audible and/or tactile information that the monitoring unit can be removed. Another feasible solution is that the monitoring unit is arranged with a manually operable switch or button that can be operated by a user. In this regard, the switch may only be operable a certain time period after the end of the dose delivery sequence. Further, the electronics circuit may be arranged with a shut-down function that will switch off the monitoring unit after it has been removed from the medicament delivery device in order to save power of the battery.

A further possibility is to control the unlocking by authentication. The authentication may be performed in a number of ways. One solution is to have a number of specific buttons or pressure sensitive areas on the user interface mechanism and wherein the user enters a specific combination or sequence of buttons in order to unlock the monitoring unit. Another type of solution not requiring any communication with external devices is the use of sensors that can identify a specific person. Such sensors include biometric sensors that e.g. can be used for finger prints or irises. Further, if a communication circuit is used, then the monitoring unit may connect to a smart device, wherein the smart device is arranged with identification and authorization software and when a user enters the correct code in the software, the smart device sends a signal to the communication circuit to unlock the monitoring unit.

A further scenario, if the monitoring unit is arranged with a communication circuit capable of communicating via radio communication networks or wifi networks, is that the monitoring unit is unlocked by an external function sending data to the monitoring unit. The external function might be a physician that is associated with the user of the medicament delivery device for monitoring adherence. The unlocking data may for example be sent when the external function receives information from the monitoring unit that the medicament delivery device has been used in accordance with a treatment schedule.

However, should the removal of the locking element fail for some reason, such as poor battery capacity or malfunction of the drive elements, a manual removal of the monitoring unit should be possible. For instance a small passage 520, FIGS. 12 and 14, may be arranged in the housing 202 of the monitoring unit, where a thin rigid rod, such as a needle or a wire tool that many smart devices are provided with for opening e.g. SIM or memory-card compartments, may be inserted. The passage is then positioned such that an insertion of the thin rod will cause its end to contact a proximal surface of the ring 500 in the first embodiment, enabling movement of the ring in the distal direction when pushing the rod. For the second embodiment, the passage may be positioned such in the housing that the end of the rod comes in contact with the proximal end of the shaft 504 of the drive element, enabling movement in the distal direction of the shaft when pushing the rod. For the third embodiment, the passage may be arranged at an angle such that the rod, when pushed, will have a force component in the circumferential direction of the locking element 514. For this embodiment, it might be necessary to push the locking element in several small steps until it is back to its initial position.

It is to be understood that the embodiments described above and shown in the drawings are to be regarded only as non-limiting examples of the disclosure and that it may be modified in many ways within the scope of the patent claims.

The invention claimed is:

1. A monitoring unit for a medicament delivery device, which monitoring unit comprises
    a housing comprising an inside surface,
    a monitoring circuit arranged in said housing, capable of detecting and monitoring functions of the medicament delivery device, and
    a tubular body positioned inside of the housing and comprising attachment tongues, where the attachment tongues are positioned circumferentially around a proximal end of the tubular body and are configured as releasable holding elements, which releasable holding elements are designed to interact with the medicament delivery device for releasably holding said monitoring unit when attached to the medicament delivery device,
    wherein a locking element is operably arranged in said monitoring unit and is designed to act on the releasable holding elements,
    wherein at least one drive element is operably connected to said locking element such that the at least one drive element causes said locking element to act on said releasable holding elements to prevent outward radial expansion of the attachment tongues and detachment of said monitoring unit from the medicament delivery device when the monitoring unit is activated.

2. The monitoring unit according to claim 1, wherein said monitoring circuit is arranged with activation elements capable of activating said monitoring unit, which activation elements are arranged to interact with said medicament delivery device such that the monitoring unit is activated when attached to said medicament delivery device.

3. The monitoring unit according to claim 1, wherein said holding elements are flexible in a generally radial direction and arranged to interact with mating holding elements on the medicament delivery device.

4. The monitoring unit according to claim 3, wherein the attachment tongues are arranged with ledges, which ledges are arranged to engage ledges of the mating holding elements.

5. The monitoring unit according to claim 3, wherein said at least one drive element moves said locking element to a blocking position when the monitoring unit is activated.

6. The monitoring unit according to claim 5, wherein said locking element is ring-shaped and arranged movable in a longitudinal direction of the monitoring unit.

7. The monitoring unit according to claim 6, wherein said at least one drive element comprises a linear actuator.

8. The monitoring unit according to claim 5, wherein said locking element is band-shaped and arranged with protrusions extending in a longitudinal direction arranged movable in a circumferential direction to blocking position wherein said protrusions block said holding elements.

9. The monitoring unit according to claim 8, wherein said at least one drive element comprises a stepper motor.

10. The monitoring unit according to claim 3, wherein said locking element is band-shaped enabling radial expansion of said locking element during attachment, where the locking element comprises end surfaces arranged with grip elements arranged to grip said drive element.

11. The monitoring unit according to claim 10 wherein the end surfaces have oppositely directed tongues, which tongues are formed as hooks, through which a movable member of said at least one drive element can extend.

12. The monitoring unit according to claim 11, wherein said at least one drive element comprises a linear actuator.

13. The monitoring unit according to claim 1, further comprising a mechanical interface arranged to interact with a mating mechanical interface arranged on the medicament delivery device, and an activation switch arranged to activate said monitoring circuit.

14. The monitoring unit according to claim 13, wherein said mechanical interface further comprises mechanical keying elements arranged with specific mechanical keying design.

15. The monitoring unit according to claim 14, wherein said mechanical keying elements comprise protrusions and recesses arranged in predetermined patterns.

16. A monitoring unit for a medicament delivery device, which monitoring unit comprises:
   a housing comprising an inside surface;
   a monitoring circuit arranged in said housing, capable of detecting and monitoring functions of the medicament delivery device;
   a tubular body positioned inside of the housing and comprising attachment tongues, where the attachment tongues are positioned circumferentially around a proximal end of the tubular body and are configured as releasable holding elements, which releasable holding elements are designed to interact with and releasably attach the monitoring unit to the medicament delivery device; and
   activation elements operatively connected to the monitoring unit, where the activation elements activate the monitoring unit when the monitoring unit is attached to the medicament delivery device,
   wherein a locking element is operably arranged in the monitoring unit and is designed to act on the releasable holding elements,
   wherein at least one drive element is operably connected to the locking element,
   wherein the at least one drive element causes the locking element to act on the releasable holding elements to prevent outward radial expansion of the attachment tongues and detachment of the monitoring unit from the medicament delivery device.

17. The monitoring unit according to claim 16, wherein the locking element is band-shaped and arranged with protrusions extending in the longitudinal direction to move in a circumferential direction to a blocking position such that the protrusions block the holding elements.

18. The monitoring unit according to claim 17 further comprising the at least one drive element that moves the locking element to the blocking position when the monitoring unit is activated.

19. The monitoring unit according to claim 16 further comprising a mechanical interface comprising mechanical keying elements arranged with specific mechanical keying design.

20. The monitoring unit according to claim 19, wherein the mechanical keying elements comprise protrusions and recesses arranged in predetermined patterns.

* * * * *